United States Patent [19]

Dreikorn et al.

[11] Patent Number: 4,670,596

[45] Date of Patent: Jun. 2, 1987

[54] DIPHENYLAMINE COMPOUNDS

[75] Inventors: Barry A. Dreikorn, Lawrence; Kenneth E. Kramer, Indianapolis, both of Ind.

[73] Assignee: Eli Lilly and Company, Indianapolis, Ind.

[21] Appl. No.: 765,423

[22] Filed: Aug. 14, 1985

Related U.S. Application Data

[62] Division of Ser. No. 519,359, Aug. 1, 1983, abandoned.

[51] Int. Cl.[4] .................... C07C 87/50; C07C 87/54
[52] U.S. Cl. .................................. 564/433; 558/418
[58] Field of Search ................ 514/658; 564/433; 260/465 E; 558/418

[56] References Cited

U.S. PATENT DOCUMENTS 4,304,791  12/1981  Clinton ............................... 424/330
4,407,820  10/1983  Dreikorn et al. ................... 564/433

FOREIGN PATENT DOCUMENTS 868165  5/1961  United Kingdom ............... 424/304

Primary Examiner—Charles F. Warren
Assistant Examiner—John A. Sopp
Attorney, Agent, or Firm—Kathleen R. S. Page; Leroy Whitaker

[57] ABSTRACT

Novel alkyl-dinitrodiphenylamine compounds are useful in controlling insects and arachnids. These compounds are useful especially in the control of citrus rust mite.

20 Claims, No Drawings

DIPHENYLAMINE COMPOUNDS

This application is a division of application Ser. No. 519,359, filed Aug. 1, 1983 abandoned.

BACKGROUND OF THE INVENTION

This invention relates to certain substituted diphenylamines, their use in controlling insects and arachnids (mites), and to compositions containing said diphenylamines. In particular, this invention relates to certin alkyl-dinitrodiphenylamines, which are active against insects and mites.

SUMMARY OF THE INVENTION

The present invention is directed to alkyl-dinitrodiphenylamines of the formula (I):

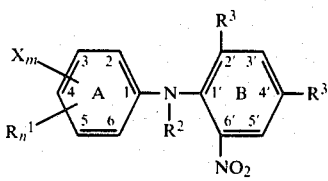

wherein:
$R^1$ is nitro, cyano, or trifluoromethyl;
$R^2$ is hydrogen or methyl;
one $R^3$ is nitro and the other $R^3$ is $C_2$–$C_6$ alkyl or $C_3$–$C_6$ cycloalkyl;
X is halo;
m is an integer of from 0 to 5; and
n is an integer of from 0 to 2;
provided that:
(a) not more than one of $R^1$ is cyano;
(b) when $R^1$ is trifluoromethyl, $R^1$ cannot also be nitro;
(c) when X is iodo, m cannot be greater than 3 and the iodos cannot be on adjacent carbons;
(d) at least one of m and n must be greater than 0, but the sum of m and n cannot be greater than 5; and
(e) $R^2$ cannot be methyl when the 2 and 6 positions of ring A are both substituted by groups other than fluorine or hydrogen.

This invention also provides a method of inhibiting the citrus rust mite which comprises applying to a locus of the mite an effective mite-inactivating amount of a compound of the formula (I). Additionally, some of the compounds also inhibit insect or arachnid populations.

Another aspect of this invention includes a formulation which comprises a compound of the formula (I) and an agriculturally-acceptable carrier therefor.

DETAILED DESCRIPTION OF THE INVENTION

Preferred compounds of this invention include those wherein $R^2$ is hydrogen and $R^3$ is tertiary butyl (t-butyl). Even more preferred are compounds wherein X is chloro, fluoro, or bromo and m is 3, while n is 0; or wherein $R^1$ is nitro and n is 2, while m is 0.

When the $R^3$ group in the para position is nitro and the $R^3$ in the ortho position is $C_2$–$C_6$ alkyl or $C_3$–$C_6$ cycloalkyl, then the compounds of formula (I) are 4,6-dinitrodiphenylamines, which also can be written as compounds of the formula (II):

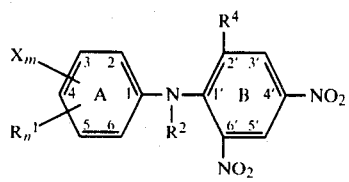

wherein
$R^1$, $R^2$, X, m, and n are defined as above and
$R^4$ is $C_2$–$C_6$ alkyl or $C_3$–$C_6$ cycloalkyl.

The 4,6-dinitro compounds of the formula (II) are preferred over compounds of the formula (III), which are 2,6-dinitrodiphenylamines:

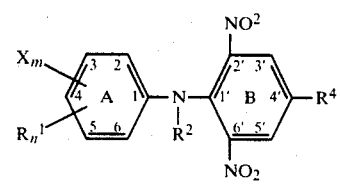

wherein $R^1$, $R^2$, X, m, n, and $R^4$ are defined above. (The 2,6-dinitrodiphenylamines are also compounds of the formula (I) when the $R^3$ group in the para position is $C_2$–$C_6$ alkyl or $C_3$–$C_6$ cycloalkyl and the $R^3$ in the ortho position is nitro.)

Preferred compounds of the formula (II) include:
2,4-dinitro-2'-t-butyl-4',6'-dinitrodiphenylamine;
2,4,6-trichloro-2'-t-butyl-4',6'-dinitrodiphenylamine;
2,4,6-tribromo-2'-t-butyl-4',6'-dinitrodiphenylamine; and
4-trifluoromethyl-2'-t-butyl-4',6'-dinitrodiphenylamine.

A preferred compound of the formula (III) is: 2,4,6-trichloro-4'-t-butyl-2',6'-dinitrodiphenylamine.

This invention also includes a method of inhibiting a citrus rust mite which comprises applying to a locus of the mite an effective mite-inactivating amount of a compound of the formula (I).

In addition, a method of inhibiting an insect or arachnid which comprises applying to a locus of the insect or arachnid an effective insect- or arachnid-inactivating amount of a compound of the formula (II) is also a part of this invention. The compounds of formula (II) are particularly useful against mites, so this invention includes a method of inhibiting a mite which comprises applying to a locus of the mite an effective mite-inactivating amount of a compound of the formula (II).

The terms used throughout this application are defined as follows.

"$C_2$–$C_6$ alkyl" refers to straight and branched aliphatic radicals of two to six carbon atoms, such as ethyl, propyl, isopropyl, butyl, tertiary-butyl (t-butyl or 1,1-dimethylethyl), pentyl, hexyl, and the like.

"$C_3$–$C_6$ cycloalkyl" refers to saturated aliphatic rings of three to six carbon atoms, such as cyclopropyl, cyclobutyl, cyclopentyl, and cyclohexyl.

"Halo" includes bromide, chloride, fluoride, and iodide.

Preparation of Compounds of Formula (I)

The compounds of this invention can be prepared by known methods. One preferred method is to react a substituted aniline derivative of the formula:

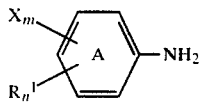

where X, R$^1$, m, and n are as defined above with a substituted dinitrochlorobenzene of the formula:

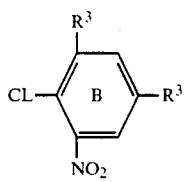

where R$^3$ is defined above. The process is carried out by reacting the aniline derivative with a base, such as sodium hydride, sodium amide, potassium amide, and the like, in an appropriate solvent, such as dimethylformamide, dimethylsulfoxide, sulfolane, acetonitrile, or tetrahydrofuran. When sodium hydride is used as the base, as is preferred, the temperature is preferably maintained at about 0° to about −20° C. The resulting aniline salt then is reacted with the substituted dinitrochlorobenzene, which first is dissolved in an appropriate organic solvent, such as dimethylformamide. The addition of the dinitrochlorobenzene is conducted from about 0° to about −20° C. After the addition, the temperature is allowed to reach room temperature. Typically the compounds of this invention are solids at room temperature and precipitate from the reaction mixture when water or ice water is added to the solution and the solution is acidified. The solid precipitate can be readily recovered by conventional techniques such as filtration and further purified, if desired, by washing and recrystallization procedures, and, where necessary, by column chromatography.

Another general method of preparing the diphenylamines of this invention comprises dissolving the appropriate substituted aniline derivative, a substituted dinitrochlorobenzene, and an acid scavenger in a solvent, such as ethanol, and refluxing the reaction mixture for a period of time sufficient to complete the reaction. Excess of the aniline derivative can function as the acid scavenger or a separate acid scavenger, such as triethylamine, sodium carbonate, or potassium carbonate, can be used, with triethylamine being preferred. The reaction mixture is refluxed from about 4 to about 48 hours, depending on the particular reactants and solvent, and then cooled. The product generally precipitates as a solid from the reaction mixture and can be recovered by filtration and further purified, if desired.

Another method of preparing the compounds of this invention is to react an unsubstituted aniline with the dinitrochlorobenzene to produce the corresponding diphenylamine and then conducting the appropriate substitution reactions, such as by nitration, to introduce the appropriate "R$^1$" substituent or substituents into the unsubstituted ring.

Still another method of preparing compounds of this invention is to N-alkylate an already-prepared diphenylamine, using such alkylating compounds as dimethyl sulfate and the like.

Aniline and substituted anilines used to prepare the compounds of this invention are known compounds and many are commercially available. The other starting component, such as, for example, 2-t-butyl-4,6-dinitrochlorobenzene, can be readily prepared from commercially available 2-t-butyl phenol by nitration and chlorination under appropriate reaction conditions. This typically is done stepwise first reacting 2-t-butyl phenol with nitric acid in a suitable reaction medium, such as 1,2-dichloroethylene. The resulting 2-t-butyl-4,6-dinitrophenol is then reacted with a halogenating agent, such as phosphorus oxychloride or thionyl chloride. The reaction preferably takes place in a suitable solvent, such as 1,2-dichloroethylene, or dimethylformamide (DMF).

The following examples illustrate the invention, but are not to be construed as limitations on it. All of the temperatures are in degrees Celsius.

2-(t-Butyl)-4,6-dinitrochlorobenzene

A solution of 1050 grams (g) of 2-t-butyl phenol dissolved in 7 liters (l) of ethylene dichloride was cooled to about −5° by placing the reaction vessel in a dry-ice-/acetone bath. Nitric acid, in the amount of 1760 g, was slowly added over a 1-hour time period to maintain the temperature between about −5° and about 0°. The reaction vessel was removed from the cooling bath and the reaction mixture was allowed to warm to room temperature and then stirred for about 16 hours. Then the reaction mixture was poured into about 12 l of stirred ice-water. About one-half of the mixture was removed and extracted with about 4 l of ether, and the ether layer was recovered. This was repeated with the remaining half of the reaction mixture and the ether layers were combined. The ether solution was extracted with water and then removed by evaporation under a vacuum, resulting in an oil residue. Ethanol was added, causing the product to precipitate. The solid precipitate was recovered and the yield was 958 g of the product: 2-t-butyl-4,6-dinitrophenol.

This product was dissolved in 3 l of ethylene dichloride and then 1840 g of phosphorus oxychloride was slowly added over a period of about 45 minutes. The temperature of the reaction mixture was maintained below about 50° by means of a water bath. After addition of the phosphorus oxychloride, the reaction mixture was heated to reflux (about 90°) and refluxed for about 40 hours. The mixture was poured into 8 l of hot water, and ice was added as required to maintain the temperature between 60° and 70°. The solution was cooled to room temperature, then extracted with ethylene dichloride, the organic layer was separated, and the water layer was extracted twice with ethylene dichloride. The extracted ethylene dichloride layers were combined, then dried over sodium sulfate-magnesium sulfate. The mixture was filtered and evaporated under vacuum to yield an oil. To this was added about 3-4 l of Skelly B, which is a petroleum fraction consisting essentially of n-hexane with a boiling range of 60°–68°. The mixture was heated to reflux, and then cooled. The product crystallized out of the solution and was recovered, giving an overall yield of 750 g [41.4 percent (%)] of 2-t-butyl-4,6-dinitrochlorobenzene. The identity of the product was confirmed by nuclear magnetic resonance (NMR) spectroscopy.

EXAMPLE 1

2-Nitro-2'-t-butyl-4',6'-dinitrodiphenylamine

Under a nitrogen atmosphere, a mixture of 10 g sodium hydride (50% oil dispersion) and 50 milliliters (ml) of DMF was cooled to between $-10°$ and $-5°$. A solution of 7.2 g (0.077 moles) of aniline in 50 ml of DMF was added over a 12-minute period, maintaining the temperature between $-5°$ and $-10°$. The reaction mixture then was stirred for about 1 hour. A solution of 20 g (0.077 moles) of 2-t-butyl-4,6-dinitrochlorobenzene in 50 ml of DMF was added slowly over a period of about 35 minutes. The reaction mixture was allowed to warm to room temperature with stirring and then the stirring was continued for about 6 hours. The reaction mixture was poured over 1.8 l of crushed ice and the volume adjusted to 1.8 l by the addition of water. The reaction mixture was acidified to below pH 4, causing a precipitate to form. The precipitate was allowed to stand for about 16 hours and then was recovered by filtration. Fractional crystallization from ethanol resulted in the desired material being isolated from the third crop of crystals. The material was further purified by recrystallization from ethanol and yielded 6.1 g of 2-t-butyl-4,6-dinitrodiphenylamine. The identity of this compound was confirmed by NMR spectroscopy.

The following elemental analysis was obtained:

Calculated for $C_{16}H_{17}N_3O_4$: Theory: C, 60.94; H, 5.43; N, 13.33; Found: C, 61.01; H, 5.23; N, 13.56.

A solution was formed by partially dissolving 4.0 g of the above diphenylamine in 100 ml of acetic acid and then 10 ml of 98% nitric acid was added over a period of about 15 minutes. After about 1 hour, 150 ml of water was added, causing a yellow precipitate to form, which was filtered from solution. There were two products in the reaction mixture and these were separated by column chromatography using silica gel as the stationary phase and toluene as the eluent. The first product to be collected from the chromatography was isolated and recrystallized from ethanol.

This product crop was identified by NMR spectroscopy as 2-nitro-2'-t-butyl-4',6'-dinitrodiphenylamine with a yield of 0.38 g (8.2%). The following elemental analysis was obtained:

Calculated for $C_{16}H_{16}N_4O_6$: Theory: C, 53.33; H, 4.48; N, 15.55; Found: C, 53.55; H, 4.74; N, 15.55.

A second product collected from the chromatography was isolated and recrystallized from ethanol.

This product was identified as 2,4-dinitro-2'-t-butyl-4',6'-dinitrodiphenylamine by NMR spectroscopy. The yield was 1.4 g (27.2%) and the following elemental analysis was obtained:

Calculated for $C_{16}H_{15}N_5O_8$: Theory: C, 47.41; H, 3.73; N, 17.28; Found: C, 47.61; H, 3.95; N, 17.45.

This second product is also prepared in Example 2 below.

EXAMPLE 2

2,4-Dinitro-2'-t-butyl-4',6'-dinitrodiphenylamine

A 57 percent oil dispersion of 40 g (0.95 moles) of sodium hydride was washed with hexanes until it was oil free, then it was covered with 900 ml of DMF and chilled to $-10°$. A solution of 169 g (0.92 moles) of 2,4-dinitroaniline in 700 ml of DMF was added in a rapid dropwise manner over 25 minutes, while the reaction temperature was held between $-10°$ and $-5°$. After the addition was completed, the reaction was stirred at $10°$ for about 1 hour. Two hundred and five grams (0.79 moles) of 2,4-dinitro-6-t-butyl-chlorobenzene was added to the mixture over a 20-minute period with the reaction temperature held between $-10°$ and $-5°$. When the addition was complete, the reaction was stirred and the temperature was allowed to reach room temperature. Then the reaction was stirred for about 16 hours at room temperature.

The reaction was warmed to $40°$ for about 1 hour, chilled to room temperature, and to it was added 20 ml of isopropyl alcohol to decompose any remaining sodium hydride. The reaction then was added dropwise to 24 l of a rapidly-stirred mixture of water and ice. The mixture was left standing for about 16 hours. A gummy material was formed, which was skimmed off the top of the aqueous layer and then pressed onto a filter. The aqueous layer was acidified to a pH of 1.0 and decanted.

NMR spectroscopy indicated that a 50/50 mixture of aniline starting material and product was present. The mixture was air dried for about 64 hours. Six liters of boiling ethanol was added and the resulting solids were filtered. The yield was 146 g (45.6%) with a melting point (MP) of $169°-172°$.

EXAMPLE 3

4-Chloro-2'-t-butyl-4',6'-dinitrodiphenylamine

In a 250 ml flask was placed 5.0 g of sodium hydride (50% oil dispersion) and 50 ml of dry DMF. The reaction mixture was cooled to between $-10°$ and $-5°$. The reaction mixture was maintained under a nitrogen atmosphere throughout the reaction.

A solution of 10.0 g (0.078 moles) of 4-chloroaniline dissolved in 50 ml of DMF was added over a period of about 10 minutes, keeping the temperature below $-5°$, and the reaction mixture was stirred for about 1 hour. A solution of 20.2 g (0.078 moles) of 2-t-butyl-4,6-dinitrochlorobenzene in 50 ml DMF was slowly added to the stirred reaction mixture over a period of about 20 minutes. The reaction mixture was allowed to warm gradually to room temperature. Total stirring time after the final addition was about 6 hours. The reaction mixture then was poured over 1.8 l of crushed ice and the volume was adjusted to 1.8 l by the addition of water. Dilute hydrochloric acid was added to acidify the mixture below pH 4 and the mixture was allowed to stand at room temperature for 48 hours. A solid precipitated, which was recovered by filtration and recyrstallized from ethanol. A total yield of 15.3 g (56.1%) was obtained with a melting point of $135°-136°$. The structure of the product as 4-chloro-2'-t-butyl-4',6'-dinitrodiphenylamine, was confirmed by infrared (IR) and NMR spectroscopy. The following elemental analysis was obtained:

Calculated for $C_{16}H_{16}N_3O_4Cl$: Theory: C, 54.94; H, 4.61; N, 12.01; Found: C, 55.14; H, 4.50; N, 12.16.

EXAMPLE 4

4-Chloro-N-methyl-2'-t-butyl-4',6'-dinitrodiphenylamine

A 500 ml flask was charged with 6.7 g (0.019 moles) of 4-chloro-2'-t-butyl-4',6'-dinitrodiphenylamine, 50 ml of acetone, 17.8 g of sodium carbonate, and 17.8 ml of dimethyl sulfate. This reaction mixture was refluxed for about 96 hours, and allowed to cool. To it was added 100 ml of water, and the mixture was heated for about 1 hour. The reaction mixture was again allowed to cool, then the flask was filled with water, and the mixture was stirred about 18 hours at room temperature. A solid precipitated from solution, which was recovered by filtration, and was purified by silica gel column chromatography, using toluene as the eluent. The product was isolated and recrystallized from ethanol. A yield of 1.4 g (20.3%) of solid product, having a melting point of 139°–140°, was obtained. NMR and IR spectroscopy was consistent with the desired product. Elemental analysis gave the following results:

Calculated for $C_{16}H_{16}N_3O_4Cl$: Theory: C, 56.13; H, 4.99; N, 11.55; Found: C, 55.90; H, 4.77; N, 11.52.

EXAMPLE 5

2,4,6-Trichloro-2'-t-butyl-4',6'-dinitrodiphenylamine

To a solution of 1050 ml of DMF and a 50% oil dispersion of 103.2 g (2.15 moles) of sodium hydride, which was held at −5° under a nitrogen atmosphere, was added 209.4 g (1.066 moles) of 2,4,6-trichloroaniline in 1050 ml of DMF. The trichloroaniline was added in a dropwise manner over a 30-minute period. Then the reaction was stirred for about 45 minutes at a temperature between −5° and 0°. Two hundred and seventy-five grams (1.06 moles) of 2-t-butyl-4,6-dinitrochlorobenzene was added dropwise over a period of 1 hour, while the temperature was maintained between −5° and 0°. The reaction was allowed to warm to room temperature and stirred for about 16 hours.

The reaction mixture was poured into about 15 l of an ice-water mixture and then acidified by the addition of hydrochloric acid with stirring. The stirring was continued for about 1 hour, keeping the reaction acidic. The reaction was left in water for about 16 hours. The precipitate that formed was filtered and dried, and then dissolved in 3.5 l of boiling ethanol. After the solution was left standing for about 16 hours, the precipitate was filtered and air dried. A yield of 273.5 g (61.7%) of crystals was obtained, with a melting point of 172°–175°. The identity of the product, 2,4,6-trichloro-2'-t-butyl-4',6'-dinitrodiphenylamine, was confirmed by NMR spectroscopy. Elemental analysis gave the following results:

Calculated for $C_{16}H_{14}N_3O_4Cl_3$: Theory: C, 45.90; H, 3.37; N, 10.04; Found: C, 46.11; H, 3.44; N, 10.14. The following examples were prepared using the same general procedures detailed above in Examples 1–5.

EXAMPLE 6

2,4,6-Trifluoro-2'-t-butyl-4',6'-dinitrodiphenylamine

Yield = 16.6 g (66.2%).
Melting point (MP) = 145°–145.5°.
NMR and IR spectroscopy were consistent with the desired product.
Molecular weight (MW) = 369.
Calculated for $C_{16}H_{14}N_3O_4F_3$: Theory: C, 52.04; H, 3.82; N, 11.38; Found: C, 51.85; H, 3.70; N, 11.26.

EXAMPLE 7

2,4,6-Tribromo-2'-t-butyl-4',6'-dinitrodiphenylamine

Yield = 7.2 g (43.5%).
MP = 187.5°–188°.
NMR and IR spectroscopy were consistent with the desired product.
MW = 552.
Calculated for $C_{16}H_{14}N_3O_4Br_3$: Theory: C, 34.81; H, 2.56; N, 7.61; Found: C, 35.05; H, 2.62; N, 7.79.

EXAMPLE 8

4-Bromo-2'-t-butyl-4',6'-dinitrodiphenylamine.

Yield = 10.1 g (65.7%).
MP = 157.5°–158°.
NMR and IR spectroscopy were consistent with the desired product.
MW = 394.
Calculated for $C_{16}H_{16}N_3O_4Br$: Theory: C, 48.75; H, 4.09; N, 10.66; Found: C, 48.99; H, 4.26; N, 10.59.

EXAMPLE 9

3,5-Bis(trifluoromethyl)-2'-t-butyl-4',6'-dinitrodiphenylamine

Yield = 13.5 g (68.0%).
MP = 155°–157°.
NMR spectroscopy was consistent with the desired product.
MW = 451.
Calculated for $C_{18}H_{15}N_3O_4F_6$: Theory: C, 47.90; H, 3.35; N, 9.31; Found: C, 49.04; H, 3.75; N, 9.37.

EXAMPLE 10

4-Trifluoromethyl-2'-t-butyl-4',6'-dinitrodiphenylamine

Yield = 5.7 g (38.2%).
MP = 158°–160°.
NMR and IR spectroscopy were consistent with the desired product.
MW = 383.
Calculated for $C_{17}H_{16}N_3O_4F_3$: Theory: C, 53.27; H, 4.21; N, 10.96; Found: C, 53.48; H, 4.34; N, 10.73.

EXAMPLE 11

2-Bromo-2'-t-butyl-4',6'-dinitrodiphenylamine

Yield = 8.2 g (53.4%).
MP = 103°–104°.
NMR and IR spectroscopy were consistent with the desired product.
MW = 394.
Calculated for $C_{16}H_{16}N_3O_4Br$: Theory: C, 48.75; H, 4.09; N, 10.66; Found: C, 48.86, H, 4.30; N, 10.84.

EXAMPLE 12

4-Iodo-2'-t-butyl-4',6'-dinitrodiphenylamine

Yield = 14.7 g (74.1%).
MP = 182.5°–183°.
NMR and IR spectroscopy were consistent with the desired product.
MW = 441.
Calculated for $C_{16}H_{16}N_3O_4I$: Theory: C, 43.56; H, 3.66; N, 9.52; Found: C, 43.71; H, 3.58; N, 9.28.

EXAMPLE 13

4-Fluoro-2'-t-butyl-4',6'-dinitrodiphenylamine

Yield = 1.6 g (12.3%).
MP = 155.5°–157°.
NMR spectroscopy was consistent with the desired product.
MW = 333.
Calculated for $C_{16}H_{16}N_3O_4F$: Theory: C, 57.66; H, 4.84; N, 12.61; Found: C, 57.88; H, 4.90; N, 12.38.

EXAMPLE 14

3,4-Dichloro-2'-t-butyl-4',6'-dinitrodiphenylamine

Yield = 13.1 g (87.5%).

MP=140°-141.5°.

NMR and IR spectroscopy were consistent with the desired product.

MW=384.

Calculated for $C_{16}H_{15}N_3O_4Cl_2$: Theory: C, 50.02; H, 3.94; N, 10.94; Found: C, 50.24; H, 4.12; N, 10.72.

EXAMPLE 15

2,6-Dibromo-2'-t-butyl-4',6'-dinitrodiphenylamine

Yield=5.9 g (31.2%).

MP=197°-198°.

NMR and IR spectroscopy were consistent with the desired product.

MW=473.

Calculated for $C_{16}H_{15}N_3O_4Br_2$: Theory: C, 40.62; H, 3.20; N, 8.88; Found: C, 40.69; H, 3.13; N, 8.76.

EXAMPLE 16

2,3-Dichloro-2'-t-butyl-4',6'-dinitrodiphenylamine

Yield=9.6 g (64.1%).

MP=192°-193°.

NMR and IR spectroscopy were consistent with the desired product.

MW=384.

Calculated for $C_{16}H_{15}N_3O_4Cl_2$: Theory: C, 50.02; H, 3.94; N, 10.94; Found: C, 49.86; H, 4.03; N, 10.93.

EXAMPLE 17

2,3,4,5,6-Pentachloro-2'-t-butyl-4',6'-dinitrodiphenylamine

Yield=5.2 g (28.1%).

MP=179.5°-180.5°.

NMR and IR spectroscopy were consistent with the desired product.

MW=487.5.

Calculated for $C_{16}H_{12}N_3O_4Cl_5$: Theory: C, 39.42; H, 2.48; N, 8.62; O, 13.13; Cl, 36.36; Found: C, 40.38; H, 2.59; N, 8.41; O, 12.03; Cl, 34.43.

EXAMPLE 18

4-Cyano-2'-t-butyl-4',6'-dinitrodiphenylamine

Yield=10.6 g (80.0%).

MP=226°-227°.

NMR and IR spectroscopy were consistent with the desired product.

MW=340.

Calculated for $C_{17}H_{16}N_4O_4$: Theory: C, 60.00; H, 4.74; N, 16.46; Found: C, 59.80; H, 4.52; N, 16.30.

EXAMPLE 19

3-Bromo-2'-t-butyl-4',6'-dinitrodiphenylamine

Yield=6.9 g (62.5%).

MP=191°-192°.

NMR and IR spectroscopy were consistent with the desired product.

MW=394.

Calculated for $C_{16}H_{16}N_3O_4Br$: Theory: C, 48.75; H, 4.09; N, 10.66; Found: C, 48.91; H, 4.05; N, 10.75.

EXAMPLE 20

3-Trifluoromethyl-2'-t-butyl-4',6'-dinitrodiphenylamine

Yield=13.6 g (91.0%).

MP=123°-124°.

NMR and IR spectroscopy were consistent with the desired product.

MW=383.

Calculated for $C_{17}H_{16}N_3O_4F_3$: Theory: C, 53.27; H, 4.21; N, 10.96; Found: C, 53.34; H, 3.95; N, 10.75.

EXAMPLE 21

2-Trifluoromethyl-2'-t-butyl-4',6'-dinitrodiphenylamine

Yield=0.99 g (6.6%).

MP=154.5°-155°.

NMR and IR spectroscopy were consistent with the desired product.

MW=383.

Calculated for $C_{17}H_{16}N_3O_4F_3$: Theory: C, 53.27; H, 4.21; N, 10.96; Found: C, 53.43; H, 4.27; N, 10.75.

EXAMPLE 22

4-Nitro-2'-t-butyl-4',6'-dinitrodiphenylamine

Yield=12.6 g (48.6%).

MP=156.5°-157.5°.

NMR and IR spectroscopy were consistent with the desired product.

MW=360.

Calculated for $C_{16}H_{16}N_4O_6$: Theory: C, 53.33; H, 4.48; N, 15.55; Found: C, 53.14; H, 4.95; N, 15.51.

EXAMPLE 23

2,4-Difluoro-2'-t-butyl-4',6'-dinitrodiphenylamine

Yield=8.2 g (30.0%).

MP=122.5°-123.5°.

NMR and IR spectroscopy were consistent with the desired product.

MW=351.

Calculated for $C_{16}H_{15}N_3O_4F_2$: Theory: C, 54.70; H, 4.30; N, 11.96; Found: C, 54.95; H, 4.25; N, 11.90.

EXAMPLE 24

2,5-Difluoro-2'-t-butyl-4',6'-dinitrodiphenylamine

Yield=12.2 g (74.0%).

MP=148°-149°.

NMR and IR spectroscopy were consistent with the desired product.

MW=351.

Calculated for $C_{16}H_{15}N_3O_4F_2$: Theory: C, 54.70; H, 4.30; N, 11.96; Found: C, 54.47; H, 4.25; N, 12.01.

EXAMPLE 25

2,4-Dichloro-2'-t-butyl-4',6'-dinitrodiphenylamine

Yield=10.2 g (68.1%).

MP=130.5°-131.5°.

NMR and IR spectroscopy were consistent with the desired product.

MW=384.

Calculated for $C_{16}H_{15}N_3O_4Cl_2$: Theory: C, 50.02; H, 3.94; N, 10.94; Found: C, 50.27; H, 3.80; N, 11.00.

EXAMPLE 26

N-Methyl-2,4-difluoro-2'-t-butyl-4',6'-dinitrodiphenylamine

Five grams (0.0142 moles) of N-(2,4-difluorophenyl)-2-(1,1-dimethylethyl)-4,6-dinitrobenzenamine, 50 ml of anhydrous acetone, 15.1 g (0.142 moles) of anhydrous sodium carbonate, and 17.9 g (0.142 moles/13.5 ml) of dimethyl sulfate were placed into a 250 ml flask. The mixture was refluxed for about 48 hours with stirring, and then allowed to sit for another 120 hours at room temperature. The reaction was refluxed again and 200 ml of water was added dropwise. After the addition of the water, the refluxing was continued for an additional hour and then the reaction mixture was allowed to cool to room temperature.

The aqueous layer was decanted from the oily layer. The oil was dissolved in methylene chloride, treated with sodium sulfate, filtered, and stripped down. The resulting residue was chromatographed on a silica gel column, using toluene/hexane (1/1) as the eluent. The appropriate fraction was collected, stripped down, dissolved in ethanol, and stripped down again.

The yield of product was 0.07 g (1.4%) and the melting point was 133°–134°. NMR spectroscopy was consistent with the desired product and Mass Spectroscopy (MS) showed the product was about 95% pure.

The following example was prepared following the same procedure as Example 26, except the final product was recrystallized from ethanol.

EXAMPLE 27

N-Methyl-4-trifluoromethyl-2'-t-butyl-4',6'-dinitrodiphenylamine

Yield = 2.98 g (54.2%).
MP = 168.5°–170°.
NMR and IR spectroscopy were consistent with the desired product.
MW = 397.
Calculated for $C_{18}H_{18}N_3O_4F_3$: Theory: C, 54.41; H, 4.57; N, 10.58; Found: C, 54.22; H, 4.46; N, 10.45.

The following examples were prepared using the same general procedures previously described in Examples 1–5.

EXAMPLE 28

2,4-Dinitro-2'-(1-methylpropyl)-4',6'-dinitrodiphenylamine

Yield = 5.6 g (51.2%).
MP = 140.5°–142°.
NMR spectroscopy was consistent with the desired product.
MW = 405.
Calculated for $C_{16}H_{15}N_5O_8$: Theory: C, 47.41; H, 3.73; N, 17.28; Found: C, 47.23; H, 3.55; N, 17.10.

EXAMPLE 29

2,4,6-Trichloro-2'-(1-methylpropyl)-4',6'-dinitrodiphenylamine

Yield = 6.04 g (57.7%).
MP = 95°–97°.
NMR spectroscopy was consistent with the desired product.
MW = 418.5.
Calculated for $C_{16}H_{14}N_3O_4Cl_3$: Theory: C, 45.90; H, 3.37; N, 10.04; Found: C, 44.15; H, 3.25; N, 9.44.

EXAMPLE 30

2,4,6-Trichloro-2'(1-methylbutyl)-4',6'-dinitrodiphenylamine

Yield = 2.81 g (28.2%).
MW = 432.5.
Calculated for $C_{17}H_{16}N_3O_4Cl_3$: Theory: C, 47.17; H, 3.73; N, 9.71; Found: C, 46.88; H, 3.82; N, 9.47.
Gas Chromatography/Mass Spectroscopy indicated 85.6% of the material was the desired isomer.

EXAMPLE 31

2,4,6-Trichloro-2'-isopropyl-4',6'-dinitrodiphenylamine

Yield = 8.05 g (79.6%).
MP = 159°–160.5°.
NMR and IR spectroscopy were consistent with the desired product.
MW = 404.5.
Calculated for $C_{15}H_{12}N_3O_4Cl_3$: Theory: C, 44.53; H, 2.99; N, 10.38; Found: C, 44.61; H, 2.94; N, 10.16.

EXAMPLE 32

2,4-Dinitro-2'-isopropyl-4',6'-dinitrodiphenylamine

Yield = 3.41 g (39.6%).
MP = 156°–158°.
NMR and IR spectroscopy were consistent with the desired product.
MW = 391.
Calculated for $C_{15}H_{13}N_5O_8$: Theory: C, 46.04; H, 3.35; N, 17.90; Found: C, 46.25; H, 3.30; N, 17.64.

EXAMPLE 33

2,4,6-Trichloro-2'-propyl-4',6'-dinitrodiphenylamine

Yield = 8.39 g (83.0%).
MP = 106°–108°.
NMR and IR spectroscopy were consistent with the desired product.
MW = 404.5.
Calculated for $C_{15}H_{12}N_3O_4Cl_3$: Theory: C, 44.53; H, 2.99; N, 10.38; Found: C, 44.63; H, 3.10; N, 10.45.

EXAMPLE 34

2,4-Dinitro-2'-ethyl-4',6'-dinitrodiphenylamine

Yield = 8.43 g (86.0%).
MP = 139°–140°.
NMR and IR spectroscopy were consistent with the desired product.
MW = 377.
Calculated for $C_{14}H_{11}N_5O_8$: Theory: C, 44.57; H, 2.94; N, 18.56; Found: C, 44.79; H, 3.00; N, 18.58.

EXAMPLE 35

2,4,6-Trichloro-2'-ethyl-4',6'-dinitrodiphenylamine

Yield = 9.9 g (97.5%).
MP = 172°–173°.
NMR and IR spectroscopy were consistent with the desired product.
MW = 390.5.
Calculated for $C_{14}H_{10}N_3O_4Cl_3$: Theory: C, 43.05; H, 2.58; N, 10.76; Found: C, 43.55; H, 2.39; N, 10.92.

EXAMPLE 36

2,4,6-Trichloro-2'-cyclohexyl-4',6'-dinitrodiphenylamine

Yield = 8.73 g (78.6%).
MP = 143°–143.5°.
NMR and IR spectroscopy were consistent with the desired product.
MW = 444.5.
Calculated for $C_{18}H_{16}N_3O_4Cl_3$: Theory: C, 48.62; H, 3.63; N, 9.45; Found: C, 48.89; H, 3.59; N, 9.47.

EXAMPLE 37

2,4,6-Trichloro-4'-t-butyl-2',6'-dinitrodiphenylamine

Yield = 9.6 g (45.0%).

MP=129°.
NMR and IR spectroscopy were consistent with the desired product.
MW=418.5.
Calculated for $C_{16}H_{14}N_3O_4Cl_3$: Theory: C, 45.90; H, 3.37; N, 10.04; O, 15.29; Cl, 25.40; Found: C, 46.10; H, 3.36; N, 10.26; O, 15.03; Cl, 25.37.

EXAMPLE 38

2-Chloro-4'-t-butyl-2',6'-dinitrodiphenylamine

Yield=16.9 g (62.0%).
MP=117°-118°.
NMR spectroscopy was consistent with the desired product.
MW=349.5.
Calculated for $C_{16}H_{16}N_3O_4Cl$: Theory: C, 54.94; H, 4.61; N, 12.01; Found: C, 55.17; H, 4.65; N, 12.04.

EXAMPLE 39

2,4,6-Tribromo-4'-t-butyl-2',6'-dinitrodiphenylamine

Yield=7.0 g (83.4%).
MP=166.5°-168°.
NMR spectroscopy was consistent with the desired product.
MW=552.
Calculated for $C_{16}H_{14}N_3O_4Br_3$: Theory: C, 34.81; H, 2.56; N, 7,61; Found: C, 34.66; H, 2.42; N, 7.64.

EXAMPLE 40

2,4-Dinitro-4'-butyl-2',6'-dinitrodiphenylamine

Yield=8.34 g (76.3%).
MP=153°-155°.
NMR and IR spectroscopy were consistent with the desired product.
MW=405.
Calculated for $C_{16}H_{15}N_5O_8$: Theory: C, 47.41; H, 3.73; N, 17.28; Found: C, 47.63; H, 3.51; N, 17.28.

EXAMPLE 41

2,4,6-Trichloro-4'-(1-methylpropyl)-2',6'-dinitrodiphenylamine

Yield=9.70 g (92.7%).
MP=144°-145°.
NMR and IR spectroscopy were consistent with the desired product.
MW=418.5.
Calculated for $C_{16}H_{14}N_3O_4Cl_3$: Theory: C, 45.90; H, 3.37; N, 10.04; Found: C, 45.98; H, 3.33; N, 9.96.

EXAMPLE 42

2,4-Dinitro-4'-ethyl-2',6'-dinitrodiphenylamine

Yield=5.88 g (80.0%).
MP=168°-169°.
NMR and IR spectroscopy were consistent with the desired product.
MW=377.
Calculated for $C_{14}H_{11}N_5O_8$: Theory: C, 44.57; H, 2.94; N, 18.56; Found: C, 44.76; H, 3.08; N, 18.40.

EXAMPLE 43

2,4,6-Trichloro-4'-propyl-2',6'-dinitrodiphenylamine

Yield=8.60 g (85.0%).
MP=139°-140°.
NMR and IR spectroscopy were consistent with the desired product.
MW=404.5.
Calculated for $C_{15}H_{12}N_3O_4Cl_3$: Theory: C, 44.53; H, 2.99; N, 10.38; Found: C, 44.55; H, 2.85; N, 10.41.

EXAMPLE 44

2,4,6-Trichloro-4'-isopropyl-2',6'-dinitrodiphenylamine

Yield=12.35 g (60.0%).
MP=111°-113°.
NMR and IR spectroscopy were consistent with the desired product.
MW=404.5.
Calculated for $C_{15}H_{12}N_3O_4Cl_3$: Theory: C, 44.50; H, 2.97; N, 10.38; O, 15.82; Cl, 26.33; Found: C, 44.47; H, 3.25; N, 10.67, O, 15.50; Cl, 26.19.

EXAMPLE 45

2,4-Dinitro-4'-pentyl-2',6'-dinitrodiphenylamine

Yield=10.19 g (90.1%).
MP=136.5°-137.5°.
NMR and IR spectroscopy were consistent with the desired product.
MW=419.
Calculated for $C_{17}H_{17}N_5O_8$: Theory: C, 48.69; H, 4.09; N, 16.70; Found: C, 48.91; H, 3.92; N, 16.65.

EXAMPLE 46

2,4,6-Trichloro-4'-(1,1-dimethylpropyl)-2',6'-dinitrodiphenylamine

Yield=9.49 g (87.8%).
MP=118.5°-119.5°.
NMR and IR spectroscopy were consistent with the desired product.
MW=432.5.
Calculated for $C_{17}H_{16}N_3O_4Cl_3$: Theory: C, 47.19; H, 3.73; N, 9.71; Found: C, 47.08; H, 3.49; N, 9.68.

EXAMPLE 47

2,4-Dinitro-4'-(1,1-dimethylpropyl)-2',6'-dinitrodiphenylamine

Yield=8.16 g (77.9%).
MP=201.5°-203°.
NMR and IR spectroscopy were consistent with the desired product.
MW=419.
Calculated for $C_{17}H_{17}N_5O_8$: Theory: C, 48.69; H, 4.06; N, 16.71; Found: C, 48.92; H, 4.23; N, 16.81.

EXAMPLE 48

2,4,6-Trichloro-4'-hexyl-2',6'-dinitrodiphenylamine

Yield=10.89 g (97.6%).
MP=90°-91.5°.
NMR and IR spectroscopy were consistent with the desired product.
MW=446.5.
Calculated for $C_{18}H_{18}N_3O_4Cl_3$: Theory: C, 48.38; H, 4.03; N, 9.41; Found: C, 48.40; H, 4.19; N, 9.20.

EXAMPLE 40

2,4-Dichloro-4'-t-butyl-2',6'-dinitrodiphenylamine

Yield=9.18 g (77.1%).
MP=155°-156°.
NMR and IR spectroscopy were consistent with the desired product.
MW=384.

Calculated for $C_{16}H_{15}N_3O_4Cl_2$: Theory: C, 50.02; H, 3.94; N, 10.94; Found: C, 49.74; H, 3.87; N, 10.77.

EXAMPLE 50

2,4,6-Trichloro-4'-butyl-2',6'-dinitrodiphenylamine

Yield=9.53 g (91.1%).
MP=127°-128°.
NMR and IR spectroscopy were consistent with the desired product.
MW=418.5.
Calculated for $C_{16}H_{14}N_3O_4Cl_3$: Theory: C, 45.90; H, 3.37; N, 10.04; Found: C, 46.05; H, 3.46; N, 9.94.

EXAMPLE 51

2,3,4,5,6-Pentachloro-4'-t-butyl-2',6'-dinitrodiphenylamine

Yield=3.73 g (75.0%).
MP=188°-190°.
NMR and IR spectroscopy were consistent with the desired product.
MW=487.5.
Calculated for $C_{16}H_{12}N_3O_4Cl_5$: Theory: C, 39.42; H, 2.48; N, 8.62; Cl, 36.36; Found: C, 39.71; H, 2.48; N, 8.43; Cl, 36.31.

EXAMPLE 52

2,4-Dinitro-4'-t-butyl-2',6'-dinitrodiphenylamine

Yield=7.75 g (70.9%).
MP=198.5°-200.5°.
NMR, IR, and mass spectroscopy were consistent with the desired product.
MW=405.
Calculated for $C_{16}H_{15}N_5O_8$: Theory: C, 47.41; H, 3.73; N, 17.28; Found: C, 47.70; H, 3.88; N, 17.27.

EXAMPLE 53

3,5-Bis(trifluoromethyl)-4'-ethyl-2',6'-dinitrodiphenylamine

Yield=10.0 g (53.7%).
MP=135°-136°.
NMR and IR spectroscopy were consistent with the desired product.
MW=423.
Calculated for $C_{16}H_{11}N_3O_4F_6$: Theory: C, 45.40; H, 2.62; N, 9.93; Found: C, 45.64; H, 2.61; N, 10.17.

EXAMPLE 54

2,4,6-Trichloro-4'-ethyl-2',6'-dinitrodiphenylamine

Yield=6.54 g (85.9%).
MP=140°-144°.
NMR and IR spectroscopy were consistent with the desired product.
MW=390.5.
Calculated for $C_{14}H_{10}N_3O_4Cl_3$: Theory: C, 43.05; H, 2.58; N, 10.76; Found: C, 43.09; H, 2.71; N, 10.94.

EXAMPLE 55

2,4-Dinitro-4'-propyl-2',6'-dinitrodiphenylamine

Yield=5.78 (54.8%).
MP=173°-175°.
NMR and IR spectroscopy were consistent with the desired product.
MW=391.
Calculated for $C_{15}H_{13}N_5O_8$: Theory: C, 46.04; H, 3.35; N, 17.90; Found: C, 46.22; H, 3.58; N, 18.01.

EXAMPLE 56

2,4,6-Trichloro-4'-pentyl-2',6'-dinitrodiphenylamine

Yield=3.70 g (34.2%).
MP=64°-65°.
NMR and IR spectroscopy were consistent with the desired product.
MW=432.5.
Calculated for $C_{17}H_{16}N_3O_4Cl_3$: Theory: C, 47.19; H, 3.73; N, 9.71; Found: C, 47.39; H, 3.72; N, 9.52.

EXAMPLE 57

2,4-Dinitro-4'-hexyl-2',6'-dinitrodiphenylamine

Yield=9.31 g (80.0%).
MP=114°-115°.
NMR and IR spectroscopy were consistent with the desired product.
MW=433.
Calculated for $C_{18}H_{19}N_5O_8$: Theory: C, 49.89; H, 4.42; N, 16.16; Found: C, 49.77; H, 4.19; N, 15.98.

EXAMPLE 58

4-Chloro-4'-t-butyl-2',6'-dinitrodiphenylamine

Ten grams (0.078 moles) of 4-chloroaniline, 100 ml of anhydrous ethanol, and 10.1 g (0.039 moles) of 2,6-dinitro-4-t-butyl-1-chlorobenzene were placed in a 250 ml flask. The reaction mixture was refluxed for about 40 hours. After the mixture was allowed to cool, a precipitate formed, was filtered, and recrystallized from ethanol.

The yield was 9.61 g (70.5%) and the melting point was 155°-156°. NMR and IR spectroscopy were consistent with the desired product.

The following elemental analysis was obtained:
Calculated for $C_{16}H_{16}N_3O_4Cl$: Theory: C, 54.94; H, 4.61; N, 12.01; Found: C, 55.16; H, 4.35; N, 12.30.

The following examples were prepared using the general procedure of Example 58.

EXAMPLE 59

4-Cyano-4'-t-butyl-2',6'-dinitrodiphenylamine

Yield=1.02 g (7.1%).
MP=211.5°-213.5°.
NMR spectroscopy was consistent with the desired product.
MW=340.
Calculated for $C_{17}H_{16}N_4O_4$: Theory: C, 60.00; H, 4.74; N, 16.46; Found: C, 59.81; H, 4.68; N, 11.25.

EXAMPLE 60

2-Fluoro-4'-t-butyl-2',6'-dinitrodiphenylamine

Yield=3.45 g (23.0%).
MP=108°-109°.
NMR spectroscopy was consistent with the desired product.
MW=333.
Calculated for $C_{16}H_{16}N_3O_4F$: Theory: C, 57.66; H, 4.84; N, 12.61; Found: C, 57.42; H, 4.71; N, 12.77.

EXAMPLE 61

4-Fluoro-4'-t-butyl-2',6'-dinitrodiphenylamine

Yield=9.0 g (75.1%).
MP=123°.
NMR and IR spectroscopy were consistent with the desired product.

MW=333.

Calculated for $C_{16}H_{16}N_3O_4F$: Theory: C, 57.66; H, 4.84; N, 12.61; Found: C, 57.36; H, 5.09; N, 12.39.

EXAMPLE 62

4-Bromo-4'-t-butyl-2',6'-dinitrodiphenylamine

Yield=4.58 g (60.2%).
MP=166°–167°.

NMR spectroscopy was consistent with the desired product.
MW=394.

Calculated for $C_{16}H_{16}N_3O_4Br$: Theory: C, 48.75; H, 4.09; N, 10.66; Found: C, 49.01; H, 4.05; N, 10.50.

EXAMPLE 63

3-Bromo-4'-t-butyl-2',6'-dinitrodiphenylamine

Yield=6.53 g (57.2%).
MP=144°–145.5°.

NMR and IR spectroscopy were consistent with the desired product.
MW=394.

Calculated for $C_{16}H_{16}N_3O_4Br$: Theory: C, 48.75; H, 4.09; N, 10.66; Found: C, 49.00; H, 4.27; N, 10.66.

EXAMPLE 64

4-Iodo-4'-t-butyl-2',6'-dinitrodiphenylamine

Yield=3.69 g (36.4%).
MP=174.5°–175.5°.

NMR and IR spectroscopy were consistent with the desired product.
MW=441.

Calculated for $C_{16}H_{16}N_3O_4I$: Theory: C, 43.56; H, 3.66; N, 9.52; Found: C, 43.76; H, 3.91; N, 9.46.

EXAMPLE 65

3-Chloro-4'-t-butyl-2',6'-dinitrodiphenylamine

Yield=7.64 g (56.1%).
MP=136.5°–138.5°.

NMR and IR spectroscopy were consistent with the desired product.
MW=349.5.

Calculated for $C_{16}H_{16}N_3O_4Cl$: Theory: C, 54.94; H, 4.61; N, 12.01; Found: C, 54.94; H, 4.66; N, 11.93.

EXAMPLE 66

3,4-Dichloro-4'-t-butyl-2',6'-dinitrodiphenylamine

Yield=0.44 g (3.7%).
MP=141°–143°.

NMR spectroscopy was consistent with the desired product.
MW=384.

Calculated for $C_{16}H_{15}N_3O_4Cl_2$: Theory: C, 50.02; H, 3.94; N, 10.94; Found: C, 53.54; H, 5.12; N, 9.28.

EXAMPLE 67

2,4-Difluoro-4'-t-butyl-2',6'-dinitrodiphenylamine

MP=79°–81°.

NMR spectroscopy was consistent with the desired product (some impurity).
MW=351.

Calculated for $C_{16}H_{15}N_3O_4F_2$: Theory: C, 54.70; H, 4.30; N, 11.96; Found: C, 54.56; H, 4.53; N, 11.75.

EXAMPLE 68

3-Trifluoromethyl-4'-t-butyl-2',6'-dinitrodiphenylamine

Yield=5.18 g (43.6%).
MP=166°–166.5°.

NMR and IR spectroscopy were consistent with the desired product.
MW=383.

Calculated for $C_{17}H_{16}N_3O_4F_3$: Theory: C, 53.27; H, 4.21; N, 10.96; Found: C, 53.48; H, 4.21; N, 10.76.

EXAMPLE 69

4-Chloro-4'-isopropyl-2',6'-dinitrodiphenylamine

Five grams (0.0204 moles) of 2,6-dinitro-4-isopropylchlorobenzene and 2.61 g (0.0204 moles) of 4-chloroaniline were dissolved in 100 ml of ethanol. Six milliliters of triethylamine was added to the solution and the reaction mixture was refluxed for about 22 hours. Afterwards, the mixture was allowed to cool and the volatiles were removed. The remaining product was washed with water, and then recrystallized from ethanol. The product yield was 1.9 g (27.8%) with a melting point of 154.5°–155°. NMR spectroscopy indicated that the desired product was formed. The molecular weight was 335.5.

The following elemental analysis was obtained:
Calculated for $C_{15}H_{14}N_3O_4Cl$: Theory: C, 53.96; H, 4.20; N, 12.52; O, 19.06; Cl, 10.56; Found: C, 53.94; H, 4.07; N, 12.61; O, 19.33; Cl, 10.61.

The following example was prepared using the general procedure of Example 69.

EXAMPLE 70

4-Trifluoromethyl-4'-t-butyl-2',6'-dinitrodiphenylamine

MP=177°–179°.

NMR and IR spectroscopy were consistent with the desired product (some impurity).
MW=383.

Calculated for $C_{17}H_{16}N_3O_4F_3$: Theory: C, 53.27; H, 4.21; N, 10.96; Found: C, 51.68; H, 4.69; N, 9.83.

EXAMPLE 71

4-Nitro-4'-t-butyl-2',6'-dinitrodiphenylamine

In a 250 ml flask was placed 5.0 g (0.0159 moles) of N-phenyl-2,6-dinitro-4-(1,1-dimethylethyl)benzenamine and 100 ml of acetic acid. The mixture was stirred for about 1½ hours and then 10 ml of 98% nitric acid was added dropwise over a period of 10 minutes. (The addition was slightly exothermic.) The mixture was stirred for about 1 hour total and then 150 ml of water was added dropwise.

A yellow precipitate formed, which was filtered and washed with water. TLC indicated the presence of 3 products, so the material was passed over a silica gel column, using toluene as the eluent. The slowest moving of the 3 spots was separated, stripped down, and recrystallized from ethanol. The yield was 1.32 g (23.1%) and the melting point was 153°–154°. NMR spectroscopy indicated that the material was the desired product. The molecular weight was 360.

The following elemental analysis was obtained:
Calculated for $C_{16}H_{16}N_4O_6$: Theory: C, 53.33; H, 4.48; N, 15.55; Found: C, 53.38; H, 4.57; N, 15.77.

The following example was prepared using the general procedure of Example 71.

EXAMPLE 72

2-Nitro-4'-t-butyl-2',6'-dinitrodiphenylamine

Yield=0.205 g (3.6%).
MP=158°–158.5°.
NMR spectroscopy was consistent with the desired product.
MW=360.
Calculated for $C_{16}H_{16}N_4O_6$: Theory: C, 53.33; H, 4.48; N, 15.55; Found: C, 53.35; H, 4.67; N, 15.34.

The present diphenylamines of the formula (II) are useful for the control of insects and arachnids. Therefore, the present invention also is directed to a method for inhibiting an insect or arachnid which comprises applying to a locus of the insect or arachnid an effective insect- or arachnid-inhibiting amount of a diphenylamine in accordance with the present invention.

The compounds of the formula (II) show activity against a number of insects and mites. The compounds show activity against Mexican bean beetle, which is a member of the insect order Coleoptera. Other members of Coleoptera include boll weevil, corn rootworm, cereal leaf beetle, flea beetles borers, Colorado potato beetle, grain beetles, alfalfa weevil, carpet beetle, confused flour beetle, powder post beetle, wireworms, rice weevil, rose beetle, plum curculio, and white grubs. The compounds also show activity against Southern armyworm, which is a member of the insect order Lepidoptera. Other typical members of this order are codling moth, cutworm, clothes moth, Indianmeal moth, leaf rollers, corn earworm, European corn borer, cabbage worm, cabbage looper, cotton bollworm, bagworm, eastern tent caterpillar, sod webworm, and fall armyworm. Some of the compounds have also shown activity against the housefly, yellow fever mosquito, and black blowfly, which are members of the order Diptera.

The compounds are useful for reducing populations of insects and mites, and are used in a method of inhibiting an insect or arachnid (mite) which comprises applying to a locus of the insect or arachnid an effective insect- or arachnid-inactivating amount of a compound of formula (II). The locus of said insects and/or mites is used herein to refer to the environment in which the insects or mites live, including the air surrounding them, the food they eat, and/or objects which they contact. For example, plant-ingesting insects or mites can be controlled by applying the active compound to plant parts, which the insects or mites eat, particularly the foliage. The compounds can be effectively used to protect textiles, paper, stored grain, or seeds by applying an active compound to such substance. The term "inhibiting an insect or arachnid" refers to a decrease in the numbers of living insects or mites. The extent of reduction accomplished by a compound depends, of course, upon the application rate of the compound, the particular compound used, and the target insect or mite species. At least an insect-inactivating or arachnid-inactivating amount should be used. The terms "insect-inactivating amount" and "arachnid-inactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite which comprises applying to a plant an effective mite-inactivating amount of a diphenylamine of the formula (II) in accordance with the present invention. The compounds are especially useful for inhibiting citrus rust mite.

Representative mite species with which the present invention can be practiced include those listed below.

| Family | Scientific Name | Common Name |
|---|---|---|
| ACARIDAE | | |
| | Aleurobius farinae | |
| | Rhizoglyphus echinopus | Bulb mite |
| | Rhizoglyphus elongatus | |
| | Rhizoglyphus rhizophagus | |
| | Rhizoglyphus sagittatae | |
| | Rhizoglyphus tarsalis | |
| ERIOPHYIDAE | | |
| | Abacarus hystrix | Grain rust mite |
| | Aceria brachytarsus | |
| | Acalitus essigi | Redberry mite |
| | Aceria ficus | |
| | Aceria fraxinivorus | |
| | Aceria granati | |
| | Aceria parapopuli | |
| | Eriophyes sheldoni | Citrus bud mite |
| | Aceria tulipae | |
| | Aculus carnutus | Peach silver mite |
| | Aculus schlechtendali | Apple rust mite |
| | Colomerus vitis | Grape erineum mite |
| | Eriophyes convolvens | |
| | Eriophyes insidiosus | |
| | Eriophyes malifoliae | |
| | Eriophyes padi | |
| | Eriophyes pruni | |
| | Epitrimerus pyri | Pear leaf blister mite |
| | Eriophyes ramosus | |
| | Erioophyes sheldoni | Citrus bud mite |
| | Eriophyes ribis | |
| | Phyllocoptes gracilis | Dryberry mite |
| | Phyllocoptruta oleivora | Citrus rust mite |
| | Phytoptus ribis | |
| | Trisetacus pini | |
| | Vasates amygdalina | |
| | Vasates eurynotus | |

-continued

| Family | Scientific Name | Common Name |
| --- | --- | --- |
| | Vasates quadripedes | Maple bladdergall mite |
| | Vasates schlechtendali | |
| EUPODIDAE | | |
| | Penthaleus major | Winter grain mite |
| | Linopodes spp. | |
| NALEPELLIDAE | | |
| | Phylocoptella avellanae | Filbert bud mite |
| PENTHALEIDAE | | |
| | Halotydeus destrustor | |
| PYEMOTIDAE | | |
| | Pyemotes tritici | Straw itch mite |
| | Siteroptes cerealium | |
| TARSONEMIDAE | | |
| | Polyphagotarsonemus latus | Broad mite |
| | Steneotarsonemus pallidus | Cyclamen mite |
| TENUIPALPIDAE | | |
| | Brevipalpus californicus | |
| | Brevipalpus obovatus | Privet mite |
| | Brevipalpus lewisi | Citrus flat mite |
| | Dolichotetranychus floridanus | Pineapple false spider mite |
| | Tenuipalpes granati | |
| | Tenuipalpes pacificus | |
| TETRANYCHIDAE | | |
| | Bryobia arborea | |
| | Bryobia practiosa | Clover mite |
| | Bryobia rubrioculus | Brown mite |
| | Eotetranychus coryli | |
| | Eotetranychus hicoriae | Pecan deaf scorch mite |
| | Eotetranychus lewisi | |
| | Eotetranychus sexmaculatus | Sixspotted spider mite |
| | Eotetranychus willametti | |
| | Eutetranychus banksi | Texas citrus mite |
| | Oligonychus ilicis | Southern red mite |
| | Oligonychus pratensis | Banks grass mite |
| | Oligonychus ununguis | Spruce spider mite |
| | Panonychus citri | Citrus red mite |
| | Panonychus ulmi | European red mite |
| | Paratetranychus modestus | |
| | Paratetranychus pratensis | |
| | Paratetranychus viridis | |
| | Petrobia latens | Brown wheat mite |
| | Schizotetranychus celarius | Bamboo spider mite |
| | Schizotetranychus pratensis | |
| | Tetranychus canadensis | Fourspotted spider mite |
| | Tetranychus cinnabarinus | Carmine spider mite |
| | Tetranychus modanieli | McDaniel spider mite |
| | Tetranychus pacificus | Pacific spider mite |
| | Tetranychus schoenei | Schoene spider mite |
| | Tetranychus urticae | Twospotted spider mite |
| | Tetranychus turkestani | Strawberry spider mite |
| | Tetranychus desertorum | Desert spider mite |

Trial 1: Mosquito Larvicide Test

Numerous compounds to be employed in the present invention were evaluated against late third- or early fourth- instar larvae of yellow fever mosquito (*Aedes aegypti*). Five-day-old larvae were allowed to feed on fresh food for at least 3 hours before starting the test. Twenty larvae were placed in one ounce paper cups each containing 25 ml of deionized water.

Formulations were prepared by dissolving 20 mg of each test compound in 2 ml of a solvent system comprising equal volumes of acetone and water and a small amount of each of Toximul R and Toximul S (Toximul R and S are each a sulfonate/nonionic emulsifier blend produced by Stepan Chemical Company, Northfield, Ill.). The resulting solution was diluted with 6 ml of distilled water. Two ml of this formulation was added to 225 ml of distilled water in a jar. The mosquito larvae in 25 ml water were added to the solution, resulting in a final solution of 250 ml, containing 20 parts per million (ppm) test compound. Results were determined 48 hours later by counting the dead and moribund larvae. The following rating code was used:

| % Dead | Rating |
| --- | --- |
| 0–10 | 0 |
| 11–20 | 1 |
| 21–30 | 2 |
| 31–40 | 3 |
| 41–50 | 4 |
| 51–60 | 5 |
| 61–70 | 6 |
| 71–80 | 7 |
| 81–90 | 8 |
| 91–100 | 9 |

The results obtained are shown in Table I.

TABLE I

| Mosquito Larvicide Test | |
| --- | --- |
| Example No. | Rating |
| 1 | 0 |
| 2 | 9 |
| 2 (at 0.1 ppm) | 0 |
| 3 | 0 |

TABLE I-continued

Mosquito Larvicide Test

| Example No. | Rating |
|---|---|
| 4 | 0 |
| 5 | 9 |
| 5(at 0.1 ppm) | 0 |
| 6 | 1 |
| 7 | 9 |
| 7(at 0.1 ppm) | 3 |
| 8 | 0 |
| 9 | 7 |
| 10 | 2 |
| 11 | 0 |
| 12 | 0 |
| 13 | 0 |
| 14 | 0 |
| 15 | 9 |
| 15(at 0.1 ppm) | 0 |
| 16 | 0 |
| 17 | 9 |
| 17(at 0.1 ppm) | 9 |
| 17(at 0.01 ppm) | 0 |
| 17(at 0.0005 ppm) | 0 |
| 18 | 0 |
| 19 | 0 |
| 20 | 0 |
| 21 | 0 |
| 22 | 9 |
| 22(at 0.1 ppm) | 0 |
| 23 | 0 |
| 24 | 0 |
| 25 | 8 |
| 28 | 9 |
| 28(at 1.0 ppm) | 6 |
| 29 | 7 |
| 29 | 3 |
| 29(at 1.0 ppm) | 0 |
| 30 | 5 |
| 31 | 0 |
| 32 | 9 |
| 33 | 0 |
| 34 | 9 |
| 34(at 0.1 ppm) | 0 |
| 35 | 0 |
| 36 | 0 |
| 36(at 1.0 ppm) | 0 |

Trial 2: Mite-Insect Screen

The novel compounds were tested for activity against Mexican bean beetle (*Epilachna varivestis*), Southern armyworm (*Spodoptera eridania*), two-spotted spider mite (*Tetranychus urticae*), melon aphid (*Aphis gossypii*), and housefly (*Musca domestica*). Each compound was formulated in essentially the same manner as set forth in the Mosquito Larvicide Test.

Mexican Bean Beetle Test

Two 4- to 6-day-old bountiful green bean primary leaves were used for each replicate in this test and 2 replications of 5 larvae each were run. The bean plants were grown in a greenhouse for 4-6 days, and then the plants were treated with test compound by spraying each with 8-10 ml of test formulation. The plants were sprayed sufficiently to thoroughly wet the entire leaf surface. When the leaves had dried, they were cut from the plants and placed in petri dishes, each of which contained 5 second-instar Mexican bean beetle larvae of uniform size. A small wad of wet cellucotton was added to each dish to help prevent the leaves from wilting. After 4 days, a mortality count for each of the 2 replications was made and a rating assigned to each test compound using the following rating scheme:

| % Dead | Rating |
|---|---|
| 0 | 0 |
| 1-50 | 1 |
| 51-99 | 2 |
| 100 | 3 |

Southern Armyworm Test

The same general test procedure as that used in the above Mexican bean beetle test was used for the Southern armyworm test. In this test 5 third-instar Southern armyworm larvae were placed in each petri dish and treated leaves were added. After 4 days, the number of dead larvae were counted and a rating was assigned for each test compound using the same rating scheme as for the Mexican bean beetle.

Two-spotted Spider Mite Test

Young Blue hubbard squash plants were thinned to 1 cotyledon per plant and infested by placing on each cotyledon a bean leaf infested with two-spotted spider mite. The plants were held for a day, then sprayed to wetting with a formulation containing 1000 ppm or lesser concentration of the test compound, with 1 infested plant (cotyledon) per treatment. Mortality was determined 4 days after treatment. A rating was assigned for each compound using the same rating scheme described above.

Housefly Contact Test

Four-day-old adult houseflies were placed in test cages with about 100 flies per cage. Each cage was sprayed with 5 ml of test formulation and then the cages were allowed to dry. Knockdown counts were made 2 hours after spraying, while mortality counts were made 24 hours after spraying and a rating was assigned to each test compound using the same rating scheme as described above. These ratings are reported as knockdown/mortality in Table II.

Melon Aphid Test

The same general test procedure as that used in the two-spotted spider mite test was used for this test, except melon aphids were utilized instead of spider mites.

The results of the mite-insect screen are reported in Table II.

TABLE II

Mite Insect Screen

| Example Number | Concentration (ppm) | Mexican Bean Beetle Repl. 1 | Mexican Bean Beetle Repl. 2 | Southern Armyworm Repl. 1 | Southern Armyworm Repl. 2 | Two-Spotted Spider Mite | Housefly Knockdown/ Mortality | Melon Aphid |
|---|---|---|---|---|---|---|---|---|
| 1 | 1000 | 1 | 0 | 0 | 0 | 0 | — | |
|   | 1000 | 1 | 1 | 0 | — | 0 | 0/0 | |
|   | 100 | 1 | 0 | 0 | — | 0 | 0/0 | |
| 2 | 1000* | 3 | 3 | 0 | 0 | 3 | — | |
|   | 1000 | 3 | 3 | 0 | — | 3 | 0/0 | |
|   | 1000 | 3 | 3 | — | — | 3 | — | |

TABLE II-continued
Mite Insect Screen

| Example Number | Concentration (ppm) | Mexican Bean Beetle | | Southern Armyworm | | Two-Spotted Spider Mite | Housefly Knockdown/ Mortality | Melon Aphid |
|---|---|---|---|---|---|---|---|---|
| | | Repl. 1 | Repl. 2 | Repl. 1 | Repl. 2 | | | |
| | 1000* | — | — | — | — | 3 | — | |
| | 1000* | — | — | — | — | 3 | — | |
| | 500 | — | — | — | — | 3 | — | |
| | 500 | — | — | — | — | 3 | — | |
| | 250 | — | — | — | — | 1 | — | |
| | 250 | — | — | — | — | 1 | — | |
| | 100 | 3 | 3 | 0 | — | 0 | 0/0 | |
| | 100 | 3 | 3 | — | — | 0 | — | |
| | 100 | 3 | 3 | — | — | — | — | |
| | 10 | 1 | 0 | — | — | — | — | |
| 3 | 1000 | 2 | 3 | 3 | 3 | 0 | — | |
| | 1000 | 2 | 2 | 3 | 3 | 0 | 0/0 | |
| | 1000 | 3 | 3 | 3 | 3 | — | — | |
| | 100 | 1 | 1 | 1 | 0 | 0 | 0/0 | |
| | 100 | 0 | 0 | 1 | 0 | — | — | |
| 4 | 1000 | 0 | 0 | 0 | 0 | 0 | — | |
| | 1000 | 1 | 1 | 0 | 0 | 0 | 0/0 | |
| | 100 | 0 | 0 | 0 | 0 | 0 | 0/0 | |
| 5 | 1000 | 3 | 3 | 3 | 3 | 0 | — | |
| | 1000 | 3 | 3 | 3 | 3 | — | 1/2 | |
| | 100 | 3 | 3 | 3 | 3 | — | — | |
| | 100 | 3 | 3 | 3 | 3 | — | 0/0 | |
| | 10 | 2 | 3 | 0 | 0 | — | — | |
| 6 | 1000 | 3 | 3 | 3 | 3 | 0 | — | |
| | 1000 | 3 | 3 | 1 | 0 | 0 | 0/0 | |
| | 100 | 3 | 3 | 0 | 0 | 0 | 0/0 | |
| | 100 | 3 | 3 | — | — | — | — | |
| | 10 | 0 | 0 | — | — | — | — | |
| 7 | 1000 | 3 | 3 | 3 | 34 | 0 | — | |
| | 1000 | 3 | 3 | 1 | 1 | 0 | 1/0 | |
| | 1000 | 3 | 3 | 3 | 3 | — | — | |
| | 100 | 3 | 3 | 0 | 0 | 0 | 0/0 | |
| | 100* | 3 | — | 0 | — | 0 | 0/0 | |
| | 100 | — | — | 0 | 0 | — | — | |
| | 100* | 3 | 3 | 0 | 0 | — | — | |
| | 100 | 3 | 3 | 0 | 0 | — | — | |
| | 50 | 3 | 3 | 0 | 0 | — | — | |
| | 25 | 3 | — | 0 | 0 | — | — | |
| | 10 | 0 | — | 0 | — | 0 | — | |
| | 10 | 0 | 0 | 0 | 0 | — | — | |
| 8 | 1000 | 1 | 1 | 3 | 3 | 0 | — | |
| | 1000 | 0 | 0 | 3 | 3 | 0 | 0/0 | |
| | 1000 | 3 | 3 | — | — | — | — | |
| | 100 | 0 | 0 | 2 | 2 | 0 | 0/0 | |
| | 100 | 0 | 0 | — | — | — | — | |
| 9 | 1000* | 3 | 3 | 3 | 2 | 3 | — | |
| | 1000 | 3 | 3 | 3 | 3 | — | —/0 | |
| | 1000 | — | — | — | — | 3 | — | |
| | 1000* | 3 | 3 | 3 | 3 | 2 | — | |
| | 100 | 0 | 0 | 0 | 0 | — | —/0 | |
| | 100 | 3 | 3 | 1 | 0 | 0 | — | |
| | 50 | — | — | — | — | 0 | — | |
| 10 | 1000 | 3 | 3 | 3 | 3 | 0 | — | |
| | 1000 | 3 | 3 | 3 | 3 | 0 | 0/0 | |
| | 1000 | 2 | 3 | 3 | 3 | — | — | |
| | 100 | 0 | 0 | 3 | 3 | 0 | 0/0 | |
| | 100 | 0 | — | 3 | — | 0 | 0/0 | |
| | 100 | — | — | 3 | 3 | — | — | |
| | 100 | 0 | 0 | 3 | 3 | — | — | |
| | 50 | 0 | 0 | 3 | 1 | — | — | |
| | 25 | 0 | — | 0 | 0 | — | — | |
| | 10 | 0 | — | 0 | — | 0 | — | |
| 11 | 1000 | 0 | 0 | — | — | 0 | — | |
| | 1000 | 3 | 3 | 0 | 0 | — | —/0 | |
| | 1000 | — | — | — | — | 0 | — | |
| | 100 | 3 | 1 | 0 | 0 | — | —/0 | |
| | 50 | — | — | — | — | 0 | — | |
| 12 | 1000 | 0 | 0 | 3 | 3 | 0 | — | |
| | 1000 | 0 | 0 | 3 | 3 | 0 | 0/0 | |
| | 1000 | — | — | 3 | 3 | — | — | |
| | 100 | 0 | 0 | 3 | 2 | 0 | 0/0 | |
| | 100 | — | — | 3 | 3 | — | — | |
| | 100 | — | — | 1 | 1 | — | — | |
| | 100 | — | — | 1 | 3 | — | — | |
| | 10 | — | — | 0 | 0 | — | — | |
| | 10 | — | — | 0 | 0 | — | — | |
| 13 | 1000 | 0 | 0 | 0 | 0 | 0 | — | |

TABLE II-continued

Mite Insect Screen

| Example Number | Concentration (ppm) | Mexican Bean Beetle Repl. 1 | Mexican Bean Beetle Repl. 2 | Southern Armyworm Repl. 1 | Southern Armyworm Repl. 2 | Two-Spotted Spider Mite | Housefly Knockdown/ Mortality | Melon Aphid |
|---|---|---|---|---|---|---|---|---|
| | 1000 | 0 | 0 | 0 | 0 | 0 | 0/0 | |
| | 100 | 0 | 0 | 0 | 0 | 0 | 0/0 | |
| 14 | 1000 | 3 | 3 | 3 | 3 | 0 | — | |
| | 1000 | 2 | 3 | 3 | 3 | 0 | 0/0 | |
| | 1000 | 1 | 2 | 3 | 3 | — | — | |
| | 100 | 0 | 0 | 3 | 3 | 0 | 0/0 | |
| | 100 | 0 | — | 3 | — | 0 | — | |
| | 100 | — | — | 3 | 3 | — | — | |
| | 100 | 0 | 0 | 0 | 0 | — | — | |
| | 50 | 0 | 0 | 2 | 0 | — | — | |
| | 25 | 1 | — | 0 | 0 | — | — | |
| | 10 | 0 | — | 0 | — | 0 | — | |
| 15 | 1000 | 3 | 3 | 1 | 0 | 3 | — | |
| | 1000 | 3 | — | 0 | — | 0 | 0/0 | |
| | 1000 | 3 | 3 | — | — | 1 | — | |
| | 100 | 2 | — | 0 | — | 0 | 0/0 | |
| | 100 | 1 | — | — | — | 0 | — | |
| 16 | 1000 | 0 | 0 | 0 | 0 | 0 | — | |
| | 1000 | 3 | 3 | 0 | 0 | — | —/0 | |
| | 1000 | — | — | — | — | 0 | — | |
| | 100 | 3 | 3 | 0 | 0 | — | —/0 | |
| | 100 | 0 | 0 | — | — | — | — | |
| | 50 | — | — | — | — | 0 | — | |
| | 10 | 0 | 0 | — | — | — | — | |
| 17 | 1000 | 3 | 3 | 3 | 3 | 0 | — | |
| | 1000 | 3 | 3 | 3 | 3 | — | —/0 | |
| | 1000 | — | — | — | — | 3 | — | |
| | 100 | 3 | 3 | 0 | 0 | — | —/0 | |
| | 50 | — | — | — | — | 0 | — | |
| 18 | 1000 | 1 | 3 | 0 | 0 | 0 | — | |
| | 1000 | 3 | 3 | 2 | 0 | — | —/0 | |
| | 1000 | — | — | — | — | 0 | — | |
| | 100 | 3 | 2 | 0 | 0 | — | —/0 | |
| | 50 | — | — | — | — | 0 | — | |
| 19 | 1000 | 0 | 1 | 0 | 0 | 0 | — | |
| | 1000 | 3 | 3 | 1 | 0 | — | —/0 | |
| | 1000 | — | — | — | — | 0 | — | |
| | 100 | 0 | 1 | 0 | 0 | — | —/0 | |
| | 50 | — | — | — | — | 0 | — | |
| 20 | 1000 | 0 | 0 | 1 | 2 | 0 | — | |
| | 1000 | 3 | 3 | 1 | 1 | — | —/0 | |
| | 1000 | — | — | — | — | 0 | — | |
| | 100 | 1 | 1 | 0 | 0 | — | —/0 | |
| | 50 | — | — | — | — | 0 | — | |
| 21 | 1000 | .2 | 1 | 0 | 0 | 0 | — | |
| | 1000 | 3 | 3 | 0 | 0 | — | —/0 | |
| | 1000 | — | — | — | — | 0 | — | |
| | 100 | 3 | 3 | 0 | 0 | — | —/0 | |
| | 100 | 3 | 2 | — | — | — | — | |
| | 50 | — | — | — | — | 0 | — | |
| | 10 | 0 | 0 | — | — | — | — | |
| 22 | 1000* | 3 | 3 | 3 | 3 | 0 | — | |
| | 1000 | 3 | 3 | — | — | — | — | |
| | 1000* | 3 | 3 | — | — | 0 | 2/2 | |
| | 1000 | 3 | 3 | — | — | — | — | |
| | 1000 | 3 | 3 | 3 | 3 | — | — | |
| | 100 | — | — | 1 | 0 | — | — | |
| | 100 | 3 | 3 | — | — | 0 | 1/1 | |
| | 100 | 3 | 3 | — | — | — | — | |
| | 100 | 3 | 3 | 1 | 0 | — | — | |
| | 100 | 3 | 3 | — | — | — | — | |
| | 100 | 3 | 3 | — | — | — | — | |
| | 10 | 1 | 0 | — | — | — | — | |
| | 10 | 0 | 0 | — | — | — | — | |
| 23 | 1000 | 3 | 3 | 0 | 0 | 0 | — | |
| | 1000 | 0 | 0 | 0 | 0 | 0 | 0/0 | |
| | 1000 | 0 | 0 | — | — | — | — | |
| | 100 | 0 | 0 | 0 | 0 | 0 | 0/0 | |
| | 100 | 0 | 0 | — | — | — | — | |
| 24 | 1000 | 0 | 2 | 0 | 0 | 0 | — | |
| | 1000 | 0 | 0 | 0 | 0 | 0 | 0/0 | |
| | 100 | 0 | 0 | 0 | 0 | 0 | 0/0 | |
| 25 | 1000 | 3 | 3 | 0 | 0 | 0 | — | |
| | 1000 | 3 | — | 1 | — | 3 | 0/0 | |
| | 1000 | 3 | 3 | — | — | — | — | |
| | 100 | 2 | — | 0 | — | 0 | 0/0 | |
| | 100 | 3 | 3 | — | — | — | — | |

TABLE II-continued

Mite Insect Screen

| Example Number | Concentration (ppm) | Mexican Bean Beetle Repl. 1 | Mexican Bean Beetle Repl. 2 | Southern Armyworm Repl. 1 | Southern Armyworm Repl. 2 | Two-Spotted Spider Mite | Housefly Knockdown/ Mortality | Melon Aphid |
|---|---|---|---|---|---|---|---|---|
| 28 | 1000* | 3 | 3 | 0 | 0 | 0 | — | 0 |
|  | 1000 | 3 | 3 | 0 | 0 | 0 | — | 0 |
| 29 | 1000* | 3 | 3 | 2 | 2 | 2 | — | 3 |
|  | 1000 | 3 | 3 | 3 | 3 | 3 | — | 1 |
|  | 1000 | 3 | 3 | — | — | — | — | — |
|  | 1000 | 3 | 3 | 3 | 2 | 3 | — | 1 |
|  | 100 | 3 | 3 | 0 | 0 | — | — | — |
|  | 100 | 3 | 3 | 0 | 0 | 0 | — | 0 |
| 30 | 1000 | 3 | 3 | 3 | 3 | 3 | — | 2 |
|  | 100 | 3 | 3 | 3 | 2 | 0 | — | 0 |
|  | 100 | 3 | 3 | 1 | 1 | 0 | 0 | 0 |
|  | 100 | 3 | 3 | — | — | — | — |  |
| 31 | 1000 | 3 | 3 | 0 | 0 | 0 | — |  |
|  | 1000 | 3 | 3 | — | — | — | — |  |
|  | 100 | 3 | 3 | — | — | — | — |  |
|  | 100 | 1 | 1 | — | — | — | — |  |
|  | 10 | 0 | 0 | — | — | — | — |  |
| 32 | 1000 | 3 | 3 | 0 | 0 | 0 | — |  |
|  | 1000 | 3 | 3 | — | — | — | — |  |
|  | 100 | 3 | 3 | — | — | — | — |  |
|  | 100 | 3 | 3 | — | — | — | — |  |
|  | 10 | 0 | 0 | — | — | — | — |  |
| 33 | 1000 | 3 | 3 | 1 | 1 | 3 | — |  |
|  | 1000 | 3 | 3 | 0 | 0 | 2 | — |  |
|  | 100 | 3 | 2 | 0 | 0 | 2 | — |  |
| 34 | 1000 | 3 | 3 | 0 | 0 | 0 | — | 0 |
|  | 1000 | 3 | 3 | — | — | — | — | — |
|  | 100 | 3 | 3 | — | — | — | — | — |
| 35 | 1000 | 2 | 1 | 0 | 0 | 0 | — | 0 |
| 36 | 1000 | 2 | 3 | 0 | 0 | 0 | — | 0 |
|  | 1000 | 3 | 3 | 0 | 0 | — | — | — |
|  | 1000 | 3 | 3 | — | — | — | — | — |
|  | 100 | 3 | 3 | — | — | — | — | — |

*phytotoxic

Trial 3: Mexican Bean Beetle and Southern Armyworm Test Insect Growth Regulator

The compounds to be tested were formulated as described above. Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm plastic petri dishes. Five second-instar Mexican bean beetle larvae and 5 second- and third-instar Southern armyworm larvae were placed in each of 3 dishes. The dishes were then placed in a room wherein the temperature and relative humidity were controlled at about 25° C. and about 51%, respectively for a period of 4 days, at which time the first evaluation of the effects of the test compounds was made. After this evaluation, 2 fresh leaves from the original treated pots were placed in each dish. The dishes were again maintained in the temperature and humidity-controlled room for an additional 3 days until the final 7-day evaluation was made.

The results were recorded by counting the number of living larvae of each species and the converting to percent control, using the following formula:

$$\% \text{ Control} = \frac{(\text{control survivors} - \text{treatment survivors})}{\text{control survivors}} \times 100$$

The results are listed in Table III.

TABLE III

| Example No. | Concentration (ppm) | Mexican Bean Beetle 4-day | Mexican Bean Beetle 7-day | Southern Armyworm 4-day | Southern Armyworm 7-day |
|---|---|---|---|---|---|
| 2 | 10 | 53 | 67 |  |  |
|  | 25 | 100 | 100 |  |  |
|  | 50 | 100 | 100 |  |  |
|  | 100 | 100 | 100 |  |  |
| 5 | 10 | 0 | 28 |  |  |
|  | 10 | 6 | 6 |  |  |
|  | 25 | 0 | 13 |  |  |
|  | 25 | 46 | 71 |  |  |
|  | 50 | 0 | 0 |  |  |
|  | 50 | 86 | 100 |  |  |
|  | 100 | 13 | 0 |  |  |
|  | 100 | 100 | 100 |  |  |
| 7 | 10 | 13 | 72 |  |  |
|  | 25 | 27 | 40 |  |  |
|  | 50 | 47 | 87 |  |  |
|  | 100 | 100 | 100 |  |  |
| 8 | 10 |  |  | 13 | 13 |
|  | 25 |  |  | 20 | 20 |
|  | 50 |  |  | 27 | 47 |
|  | 100 |  |  | 33 | 93 |
|  | 10 |  |  | 0 | 0 |
|  | 25 |  |  | 0 | 0 |
|  | 50 |  |  | 0 | 0 |
|  | 100 |  |  | 7 | 47 |
| 10 | 10 |  |  | 0 | 0 |
|  | 25 |  |  | 7 | 0 |
|  | 50 |  |  | 0 | 13 |
|  | 100 |  |  | 0 | 47 |
| 11 | 10 | 0 | 13 | 0 | 0 |
|  | 25 | 0 | 33 | 0 | 0 |
|  | 50 | 0 | 60 | 0 | 0 |
|  | 100 | 0 | 53 | 0 | 0 |
| 14 | 10 |  |  | 7 | 0 |
|  | 25 |  |  | 0 | 0 |
|  | 50 |  |  | 0 | 0 |
|  | 100 |  |  | 0 | 0 |

TABLE III-continued

| Example No. | Concentration (ppm) | Mexican Bean Beetle 4-day | Mexican Bean Beetle 7-day | Southern Armyworm 4-day | Southern Armyworm 7-day |
|---|---|---|---|---|---|
| 18 | 10 | 0 | 0 | | |
|  | 25 | 0 | 0 | | |
|  | 50 | 0 | 0 | | |
|  | 100 | 0 | 0 | | |

Trial 4: Blowfly Larvae and Adult Housefly Test

Representative compounds to be employed in accordance with the present invention were evaluated against larvae of blowfly (*Phormia regina*) and against adult housefly (*Musca domestica*).

The test was conducted as follows: one milliliter of DMF was added to 1 mg of compound in a 15 ml test tube, and then 9 ml of distilled water was added. A 0.2 ml portion of this stock solution was placed in a 6.5 ml test tube and 1.8 ml of bovine serum was added, yielding a 10 ppm test solution. To obtain a 20 ppm test solution, the amount of test compound was increased accordingly. A dental wick was placed in the test tube and approximately 40 to 50 blowfly larvae were placed on the wick. The test tube was covered with a cotton ball and incubated at 27° C. for 24 hours, at which time larval mortality counts were made. Efficacy was calculated as follows:

$$\frac{\text{total larval population} - \text{no. live larvae}}{\text{total larval population}} \times 100$$

(larval population was adjusted for normal mortality in the control).

Ratings were made according to the following scale:
0 = none dead
1 = <50% dead
2 = 51–75% dead
3 = 76–90% dead
4 = 91–99% dead
5 = 100% dead The test against the adult housefly was conducted by the same procedure, except that the saturated wick was placed in a petri dish and approximately 25 chilled houseflies were added. The dish then was covered and incubated at 27° C. and 70% relative humidity.

The results of these tests are shown in Tables IV and IVA.

TABLE IV

| Example No. | Blowfly Larvae Concentration (ppm) | Rating |
|---|---|---|
| 1 | 10 | 0 |
| 2 | 10 | 0 |
|  | 20 | 5 |
|  | 40 | 5 |
|  | 60 | 5 |
|  | 100 | 5 |
| 3 | 10 | 0 |
| 4 | 10 | 0 |
| 5 | 10 | 0 |
| 6 | 10 | 0 |
| 7 | 10 | 0 |
| 8 | 10 | 0 |
| 9 | 10 | 0 |
|  | 10 | 5 |
| 10 | 10 | 0 |
| 11 | 10 | 0 |
| 12 | 10 | 0 |
| 13 | 10 | 0 |

TABLE IV-continued

| Example No. | Blowfly Larvae Concentration (ppm) | Rating |
|---|---|---|
| 14 | 10 | 0 |
| 15 | 10 | 0 |
| 16 | 10 | 0 |
| 17 | 10 | 0 |
| 18 | 10 | 0 |
| 19 | 10 | 0 |
| 20 | 10 | 0 |
| 21 | 10 | 0 |
| 22 | 10 | 0 |
| 23 | 10 | 0 |
| 24 | 10 | 0 |
| 25 | 10 | 0 |
| 28 | 20 | 0 |
| 29 | 20 | 0 |
| 30 | 30 | 0 |
|  | 50 | 0 |
| 31 | 20 | 0 |
|  | 40 | 0 |
| 32 | 20 | 5 |
|  | 20 | 0 |
|  | 40 | 5 |
| 33 | 20 | 0 |
|  | 40 | 0 |
| 34 | 50 | 0 |
| 35 | 50 | 0 |
| 36 | 20 | 0 |

TABLE IVA

| Example No. | Adult Housefly Concentration (ppm) | Rating |
|---|---|---|
| 2 | 20 | 2 |
|  | 40 | 3 |
|  | 60 | 3 |
|  | 100 | 3 |
| 9 | 10 | 4 |
| 32 | 20 | 5 |

Trial 5: Two-Spotted Spider Mite Test

In this test, the compounds were tested against the two-spotted spider mite. All but one of the leaves from 10-day-old Kentucky Wonder bean plants were removed. The remaining leaf was infested with two-spotted spider mites (*Tetranychus urticae*) by contacting it with a mite-infested leaf from another plant. The leaves were maintained in contact for 1–2 days to allow the mites to transfer to the bean plant leaf.

Formulations of test compounds were prepared by dissolving 10 mg of each compound in 1 ml of a solvent system, consisting of equal volumes of acetone and ethanol and small amounts of Toximul R and Toximul S (equivalent to a concentration of 23 gm/l and 13 gm/l, respectively). The resulting solution was diluted with 9 ml of water to give 10 ml of solution, containing 1000 ppm of test compound. The solution was further diluted, where necessary, to give the concentration of test compound shown in the Table V. [In two tests, a compound was formulated as an emulsifiable concenrate, (EC)].

The newly infested bean leaf was sprayed to the point of run-off with 5 ml of test formulation. Spraying was done using an atomizer and the plants were maintained in the laboratory for 1–3 days. The effectiveness of the test compound against mites was determined by counting the number of mites surviving in a microscope field of 6.28 square centimeters (sq. cm). If more than 25 mites existed in this area of the leaf, counting was stopped at 25 and this number was recorded. In each test a control plant was treated with solvent and the number of mites counted at the end of the test period to insure that at least 25 mites were present on the control leaf.

Four replicates were conducted and the results were recorded as the mean.

Plant injury ratings were generally made, on the following scale:
 0 = no injury
 1 = slight injury
 2 = moderate injury
 3 = severe injury The results of this trial are reported in Table V.

TABLE V

| Example Number | Two-Spotted Spider Mite Concentration (ppm) | Mean | Plant Injury Rating |
|---|---|---|---|
| 2 | 1000 | 21.5 | 0.5 |
|   | 100 | 25.0 | 0 |
|   | 50 | 25.0 | 0 |
|   | 25 | 25.0 | 0.3 |
|   | 10 | 25.0 | 0 |
| 2 | 100 | 4.0 | 0 |
|   | 50 | 5.5 | 0 |
| 2 | 1000 | 5.8 | 1.3 |
|   | 100 | 12.3 | 0 |
|   | 50 | 20.0 | 0 |
| 2 | 1000 | 0.0 | 2.5 |
|   | 100 | 0.0 | 0.3 |
|   | 50 | 0.0 | 0 |
| 2 (1 EC) | 1000 | 0.8 | 1.0 |
|   | 100 | 25.0 | 0 |
|   | 50 | 24.3 | 0.3 |
| 2 (1 EC) | 1000 | 8.0 | 0.3 |
|   | 100 | 14.5 | 0 |
|   | 50 | 8.8 | 0 |
| 2 | 1000 | 0.0 | 0 |
|   | 100 | 1.3 | 0 |
|   | 50 | 3.3 | 0 |
| 2 | 1000 | 1.5 | 0 |
|   | 100 | 25.0 | 0 |
|   | 50 | 25.0 | 0 |
| 3 | 1000 | 25.0 | 0 |
|   | 100 | 25.0 | 0 |
|   | 50 | 25.0 | 0 |
| 3 | 1000 | 25.0 | 0 |
|   | 100 | 25.0 | 0 |
|   | 50 | 25.0 | 0 |
| 3 | 1000 | 25.0 | 0 |
|   | 100 | 25.0 | 0 |
|   | 50 | 25.0 | 0 |
| 5 | 1000 | 0.0 | 2.8 |
|   | 100 | 0.0 | 0.8 |
|   | 50 | 0.0 | 0.8 |
| 5 | 1000 | 0.5 | 1.0 |
|   | 100 | 1.0 | 0 |
|   | 50 | 2.8 | 0 |
|   | 25 | 12.5 | 0 |
|   | 10 | 22.0 | 0 |
| 6 | 1000 | 20.3 | 0 |
|   | 100 | 21.5 | 0 |
|   | 50 | 25.0 | 0 |
|   | 25 | 25.0 | 0 |
|   | 10 | 25.0 | 0 |
| 6 | 1000 | 0.0 | 0 |
|   | 100 | 0.0 | 0 |
|   | 50 | 2.8 | 0 |
| 7 | 1000 | 1.5 | 0 |
|   | 100 | 20.0 | 0 |
|   | 50 | 21.0 | 0 |
| 7 | 1000 | 10.5 | 0 |
|   | 100 | 20.5 | 0 |
|   | 50 | 23.3 | 0 |
| 8 | 1000 | 25.0 | 0 |
|   | 100 | 25.0 | 0 |
|   | 50 | 25.0 | 0 |
| 8 | 1000 | 25.0 | 0 |
|   | 100 | 25.0 | 0 |

TABLE V-continued

| Example Number | Two-Spotted Spider Mite Concentration (ppm) | Mean | Plant Injury Rating |
|---|---|---|---|
|   | 50 | 25.0 | 0 |
| 11 | 1000 | 25.0 | 0 |
|   | 100 | 25.0 | 0 |
|   | 50 | 25.0 | 0 |
| 11 | 1000 | 25.0 | 0 |
|   | 100 | 25.0 | 0 |
|   | 50 | 25.0 | 0 |
| 12 | 1000 | 25.0 | 0 |
|   | 100 | 25.0 | 0 |
|   | 50 | 25.0 | 0 |
| 12 | 1000 | 25.0 | 0 |
|   | 100 | 25.0 | 0 |
|   | 50 | 25.0 | 0 |
|   | 25 | 25.0 | 0 |
|   | 10 | 25.0 | 0 |
| 13 | 1000 | 25.0 | 0 |
|   | 100 | 25.0 | 0 |
|   | 50 | 25.0 | 0 |
|   | 25 | 25.0 | 0 |
|   | 10 | 25.0 | 0 |
| 13 | 1000 | 25.0 | 0 |
|   | 100 | 25.0 | 0 |
|   | 50 | 25.0 | 0 |
| 14 | 1000 | 25.0 | 0 |
|   | 100 | 25.0 | 0 |
|   | 50 | 25.0 | 0 |
| 14 | 1000 | 24.8 | 0 |
|   | 100 | 25.0 | 0 |
|   | 50 | 25.0 | 0 |
|   | 10 | 25.0 | 0 |
| 15 | 1000 | 25.0 | 0 |
|   | 100 | 25.0 | 0 |
|   | 50 | 25.0 | 0 |
| 16 | 1000 | 25.0 | 0 |
|   | 100 | 25.0 | 0 |
|   | 50 | 25.0 | 0 |
| 16 | 1000 | 25.0 | 0 |
|   | 100 | 25.0 | 0 |
|   | 50 | 25.0 | 0 |
| 18 | 1000 | 25.0 | 0 |
|   | 100 | 25.0 | 0 |
|   | 50 | 25.0 | 0 |
| 19 | 1000 | 25.0 | 0 |
|   | 100 | 25.0 | 0 |
|   | 50 | 25.0 | 0 |
| 20 | 1000 | 25.0 | 0 |
|   | 100 | 25.0 | 0 |
|   | 50 | 25.0 | 0 |
| 20 | 1000 | 25.0 | 0 |
|   | 100 | 25.0 | 0 |
|   | 50 | 25.0 | 0 |
| 21 | 1000 | 25.0 | 0 |
|   | 100 | 25.0 | 0 |
|   | 50 | 25.0 | 0 |
| 21 | 1000 | 25.0 | 0 |
|   | 100 | 25.0 | 0 |
|   | 50 | 25.0 | 0 |
| 21 | 1000 | 25.0 | 0 |
|   | 100 | 25.0 | 0 |
|   | 50 | 25.0 | 0 |
| 23 | 1000 | 25.0 | 0 |
|   | 100 | 25.0 | 0 |
|   | 50 | 25.0 | 0 |
| 24 | 1000 | 25.0 | 0 |
|   | 100 | 25.0 | 0 |
|   | 50 | 25.0 | 0 |
| 24 | 1000 | 25.0 | 0 |
|   | 100 | 25.0 | 0 |
|   | 50 | 25.0 | 0 |
| 28 | 1000 | 25.0 | 0 |
|   | 100 | 25.0 | 0 |
|   | 50 | 25.0 | 0 |
| 29 | 1000 | 22.75 | 0 |
|   | 100 | 25.0 | 0 |
|   | 50 | 25.0 | 0 |
| 36 | 1000 | 25.0 | 0 |
|   | 100 | 25.0 | 0 |

TABLE V-continued

| Example Number | Two-Spotted Spider Mite | | |
|---|---|---|---|
| | Concentration (ppm) | Mean | Plant Injury Rating |
| | 50 | 25.0 | 0 |

Trial 6: Resistant Two-Spotted Spider Mite Test

A few of the compounds to be employed in accordance with the present invention were simultaneously evaluated for the control of 2 strains of two-spotted spider mites, the first strain of normal susceptibility (the same strain as used in the preceding experiments), and the second strain known to be resistant to standard organophosphate and carbamate toxicants. The evaluation was carried out as set forth in the test procedures described immediately preceding in Table V. The test results were as set forth in the following table: Table VI.

TABLE VI

| Example Number | Two-Spotted Spider Mite | | | |
|---|---|---|---|---|
| | Concentration (ppm) | Mean of Susceptible Mites | Mean of Resistant Mites | Plant Injury Rating |
| 2 | 1000 | 1.0 | 4.5 | 1.0 |
| | 100 | 16.5 | 16.3 | 0 |
| | 10 | 25.0 | 25.0 | 0 |
| 2 | 1000 | 0.0 | 0.0 | — |
| | 100 | 0.8 | 9.0 | — |
| | 10 | 2.5 | 6.0 | — |
| 2 | 1000 | 0.3 | 3.0 | — |
| | 100 | 8.8 | 4.0 | — |
| | 50 | 13.3 | 18.8 | — |

Trial 7: Two-Spotted Spider Mite Ovicide Test

Various compounds were evaluated for ovicidal activity against the two-spotted spider mite. Circles of 1 cm diameter are cut in infested bean leaves. (The infestation must be at least 10 eggs per circle). The circles of leaf tissue were dipped in a solution of 95 percent ethanol and 5 percent water for 90 seconds, then rinsed with water, and allowed to dry for 1 hour. The tissue was dipped into the test compound solution for 2 seconds and the lower leaf surface was placed face up on agar in a petri dish (Two ppm of merthiolate was added to the agar to prevent fungal infection.)

The petri dishes were set under a 24-hour light cycle and covered with a plastic sheet allowing slight air circulation. Newly hatched nymphs were counted 2–3 days after treatment. The percent control was calculated and the results are recorded in Table VII.

TABLE VII

| Example Number | Two-Spotted Spider Mite Ovicide Test | |
|---|---|---|
| | Concentration (ppm) | Percent Control |
| 2 | 100 | 100 |
| | 50 | 100 |
| | 25 | 100 |
| | 10 | 100 |
| 7 | 100 | — |
| | 50 | 100 |
| | 25 | 48 |
| | 10 | — |
| 8 | 100 | 73 |
| | 50 | 50 |
| | 25 | 0 |
| | 10 | — |

TABLE VII-continued

| Example Number | Two-Spotted Spider Mite Ovicide Test | |
|---|---|---|
| | Concentration (ppm) | Percent Control |
| 10 | 100 | — |
| | 50 | 41 |
| | 25 | 7 |
| | 10 | — |
| 18 | 100 | — |
| | 50 | 81 |
| | 25 | 26 |
| | 10 | — |

Trial 8: Two-Spotted Spider Mite Test-Soybean

The compound of Example 2 was foliar applied to soybeans at rates of 0.5, 1, and 2 pounds per acre (lb/A) in a spray volume of 100 gallons per acre (gal/A). Plot size consisted of 2 rows of soybeans, 20 feet long, and 4 replicates were done for each treatment. Mite counts were made on 10 leaves taken at random from each plot. Each leaf was placed under a dissecting microscope and the total number of living mites observed in a 0.5 inch field at the base of the leaf adjacent to the midrib was recorded. The results were recorded as percent control in Table VIII. Some crop injury was observed at 1 and 2 lb/A when the compound was applied as an emulsifiable concentrate. [The compound also was applied as a wettable powder (W).]

TABLE VIII

| Example Number | Two-Spotted Spider Mite-Soybean | | |
|---|---|---|---|
| | Concentration (lb/A) | Percent Control Days after Treatment | |
| | | 2 | 6 |
| 2 (50W) | 0.5 | 18.8 | 0.0 |
| | 1 | 71.3 | 28.0 |
| | 2 | 45.2 | 32.7 |
| 2 (1EC) | 0.5 | 79.2 | 17.5 |
| | 1 | 76.7 | 60.6 |
| | 2 | 89.4 | 50.4 |

Phytotoxicity was observed with the 1 EC formulation at the following rates and days after treatment:

| Rate (lb/A) | Days After Treatment |
|---|---|
| 1 | 9 |
| 2 | 5 |
| 2 | 9 |

Trial 9: Two-Spotted Spider Mite Test-Eggplant

The compound of Example 2 was foliar applied at rates of 0.5, 1, 2, and 2.5 lb/A to a young eggplant (*Solanum melongena* var. *esculentum*) crop having a moderate infestation of two-spotted spider mites. The first 3 applications were made at weekly intervals with a small plot spray machine using a spray system equipped with a 3-nozzle boom, applying a spray volume of 100 gal/A. The last 2 treatment applications were made at 2-week intervals using the same equipment but with a total of 5 spray nozzles to achieve full coverage of the rapidly growing plants. Three plants in each of the 20-foot treatment plots were flagged and live adult mites on the entire plant or a given number of leaves were counted both pretreatment and at various evaluation dates.

After the second application, the eggplant foliage was moderately infested with tomato pinworm (*Keiferia lycopersicella*). The results are shown in Table IX.

Slight to moderate foliar injury was evident at 1 lb/A and above, 5 days after the second application. The injury was a necrotic spotting on the underside of the leaves. This injury remained on the foliage, but did not increase in severity and new injury was not evident with additional treatments.

TABLE IX

Two-Spotted Spider Mite-Eggplant

| Example Number | Concentration (lb/A) | Percent Control Days After First Treatment | | | | |
|---|---|---|---|---|---|---|
| | | 7[a] | 12[b] | 19 | 26 | 40 |
| 2 (1 EC) | 0.5 | 74.1 | 65.8 | 76.3 | 75.6 | 51.9 |
| | 1 | 84.3 | 67.5* | 87.7* | 74.0 | 62.2 |
| | 2 | 73.3 | 80.9* | 82.0* | 70.3 | 86.3 |
| | 2.5 | 91.8 | 90.8* | 94.0* | 92.2 | 87.0 |

[a]Second treatment.
[b]Third treatment.
*Foliar injury.

Trial 10: Two-Spotted Spider Mite Field Test—Mung Bean

The compound of Example 2 was field tested for protection of mung beans against the two-spotted spider mite. Formulations were prepared by dissolving an emulsifiable concentrate of this compound in sufficient water to provide application rate of 0.5, 1, 2, and 2.5 lb/A (1 to 5 lb/100 gal) in a spray volume of 50 gal/A. The formulation was added to a sprayer utilizing compressed air as the propellant equipped with a boom having 6 nozzles. Two rows of mung beans, each row being about 20 feet long, were considered 1 plot and treatment of 4 such plots constituted 4 replications. The plots were sprayed with the test formulation. Two days after treatment, the first evaluation was made by removing a leaf from the treated mung bean plants, placing it under a dissecting microscope, and counting the number of living mites in a 0.5 inch field adjacent to the leaf midrib.

Two days following treatment the compound did not provide satisfactory control at rates up to 2.5 lb/A and resulted in some crop injury at rates above 1 lb/A.

Trial 11: Two-Spotted Spider Mite Test—Bush Bean

Various compounds were formulated as described in previous trials. Fifty to 100 two-spotted spider mites (adults, nymphs, and larvae) were introduced on bush bean leaves (Phaseolus sp), which had the primary leaves cut to an area of approximately 1 sq. in. After the mites established themselves on the undersurface of the leaf (about 1 hour), they were sprayed with 5 ml of compound formulation, using 1 leaf for each of 4 replications.

Ovicidal activity was determined by introducing the mites (gravid females) on the leaves and allowing them to oviposit for 3 days. Mobile forms were removed by dipping the leaves in a 95% ethanol solution for 90 seconds. After the leaves were rinsed and dried, the eggs were sprayed with 5 ml of compound formulation.

Ovicidal activity was evaluated 4 days after treatment. For contact activity on mobile forms, observations were made at 1 day after treatment. The following Table XI records the results as percent mortality.

TABLE XI

Two-Spotted Spider Mite - Bush Bean

| Example Number | Concentration (ppm) | Percent Control | |
|---|---|---|---|
| | | Mobile | Ovicide |
| 2 | 100 | 91.5 | 39.0 |
| | 50 | 86.5 | 23.5 |
| | 10 | 91.0 | 13.0 |
| 6 | 100 | 98.0 | 42.5 |
| | 50 | 99.0 | 31.0 |
| | 10 | 75.0 | 26.0 |
| 7 | 100 | 98.0 | 5.5 |
| | 50 | 87.0 | 4.0 |
| | 10 | 36.5 | 4.5 |
| 11 | 100 | 12.5 | 40.0 |
| | 50 | 4.0 | 40.0 |
| | 10 | 3.5 | 11.0 |
| 27 | 2000 | 29.3 | |
| 31 | 2000 | 100.0 | |
| 33 | 1000 | 97.0 | |
| | 100 | 100.0 | |
| | 100 | 71.0 | |
| | 50 | 46.3 | |
| | 25 | 21.0 | |

Trial 12: Two-Spotted Spider Mite Test—Bountiful Bean

Compounds of this invention were evaluated against two-spotted spider mites on Bountiful-variety beans. The mites were introduced on a 2-cm disk of bean leaf and then the leaf was dipped into a solution of compound as described in Trial 7. The number of mites were counted two days following treatment and the results were recorded as means in Table XII.

TABLE XII

Two-Spotted Spider Mite Bountiful Bean

| Example Number | Concentration (ppm) | Mean |
|---|---|---|
| 2 | 1000 | 0.00 |
| | 300 | 0.00 |
| | 100 | 0.00 |
| | 50 | 0.67 |
| | 25 | 2.00 |
| | 10 | 0.33 |
| | 5 | 0.67 |
| 5 | 1000 | 0.00 |
| | 300 | 0.00 |
| | 100 | 0.00 |
| | 50 | 2.67 |
| | 10 | 17.67 |
| 7 | 1000 | 0.00 |
| | 300 | 14.67 |
| | 100 | 25.00 |
| | 10 | 25.00 |
| 14 | 1000 | 17.33 |
| | 300 | 25.00 |
| | 100 | 25.00 |
| | 10 | 25.00 |
| 25 | 1000 | 0.00 |
| | 300 | 1.33 |
| | 100 | 25.00 |
| | 10 | 25.00 |

Trial 13: Citrus Rust Mite Test—Temple Orange

An emulsifiable concentrate of the compound of Example 2 was diluted with sufficient water to provide a formulation giving a rate of application of 2 lb/A when applied from a sprayer unit with a single nozzle hand held boom to achieve a full-coverage foliar spray of 1000 gal/A. A 5-foot Temple orange tree (*Citrus sinensis*) heavily infested with citrus rust mites (Phyllocoptruta oleivora) was selected for treatment. Each half of the tree was designated as 1 of 2 experimental replications. Twenty leaves (10 leaves from each half of the tree), having a mite population in excess of 50 to 100 citrus rust mites, were marked for evaluation after treatment. The tree was then sprayed with the test formulation providing treatment at a rate of 2 lb/A. At the end of 1, 4, 7, 19, and 32 days some of the pretagged, treated leaves were collected and examined under a microscope. The number of live mites on 2-4 leaves were counted with a surface area of from about 600-800 square millimeters (sq. mm). The percent control of the mite population was calculated, giving the following results in Table XIII.

TABLE XIII

Citrus Rust Mite - Temple Orange

| Example Number | Concentration (lb/A) | Percent Control Days After Treatment | | | | |
|---|---|---|---|---|---|---|
| | | 1 | 4 | 7 | 19 | 32 |
| 2 | 2 | 99.2 | 92.4 | 97.1 | 99.3 | 83.6 |

Trial 14: Citrus Rust Mite Test—Temple Orange

Emulsifiable concentrates of various compounds were applied to Temple orange trees to achieve a foliar spray of 500 gal/A. Four days after treatment, the number of live mites were counted on 15 leaves selected at random from each of 3 single-tree replications. The total surface area for each replication is 6,000 sq. mm. Thirteen days after treatment, the number of live mites were counted on 5 fruit per replication. The results are recorded as percent control in Table XIV.

TABLE XIV

Citrus Rust Mite - Temple Orange

| Example Number | Concentration (ppm) | Percent Control Days After Treatment | |
|---|---|---|---|
| | | 4 | 13 |
| 2 | 100 | 90.2 | 94.8 |
| | 200 | 95.3 | 77.3 |
| | 500 | 97.3 | 97.2 |
| 5 | 100 | 92.0 | 80.4 |
| | 200 | 95.9 | 85.2 |
| | 500 | 93.8 | 91.8 |
| 7 | 100 | 85.8 | 77.1 |
| | 200 | 80.0 | 86.0 |
| | 500 | 97.6 | 67.5 |
| 10 | 100 | 92.4 | 52.7 |
| | 200 | 89.2 | 31.7 |
| | 500 | 93.0 | 66.5 |
| 37 | 100 | 72.0 | 44.9 |
| | 200 | 93.6 | 65.9 |
| | 500 | 93.5 | 48.9 |

Trial 15: Citrus Rust Mite Test—Hamlin Orange

The compounds of Example Nos. 2 and 10 were formulated as emulsifiable concentrates and foliar applied to Hamlin-variety orange trees infested with citrus rust mites. Ten gallons of the compound solution were applied to each tree. Three replications were run with the number of mites counted on 5 leaves for each replication on days 5 or 6 and 14 or 15, while 20 leaves were used on days 29 or 32, and 10 leaves were counted on day 49 or 50. The results were recorded as percent control in Table XV.

TABLE XV

Citrus Rust Mite - Hamlin Orange

| Example Number | Concentration (ppm) | Percent Control Days After Treatment | | | |
|---|---|---|---|---|---|
| | | 5-6 | 14-15 | 29-30 | 49-50 |
| 2 | 50 | 92.3 | 65.9 | 2.5 | 3.5 |
| 2 (1 EC) | 150 | 0.0 | 41.8 | 9.1 | 3.7 |
| | 100 | 67.4 | 53.8 | 7.8 | 3.6 |
| | 75 | 35.7 | 16.5 | 26.0 | 3.3 |
| | 50 | 64.3 | 0.0 | 10.4 | 3.9 |
| 7 (1 EC) | 150 | 40.7 | 0.0 | 2.6 | 3.9 |
| | 100 | 57.5 | 8.8 | 5.2 | 3.3 |
| | 75 | 4.5 | 0.0 | 2.6 | 3.4 |
| | 50 | 9.9 | 13.2 | 36.4 | 3.3 |
| 10 | 50 | 86.4 | 83.5 | 1.8 | 2.9 |
| 10 (1 EC) | 150 | 82.3 | 42.8 | 27.3 | 3.0 |
| | 100 | 90.5 | 64.8 | 22.1 | 3.1 |
| | 75 | 63.3 | 19.8 | 7.8 | 3.4 |
| | 50 | 58.4 | 33.0 | 10.4 | 3.5 |
| 37 (1 EC) | 150 | 76.9 | 0.0 | 0.0 | 3.7 |
| | 100 | 36.6 | 36.3 | 3.9 | 3.5 |
| | 75 | 9.0 | 11.0 | 11.7 | 3.0 |
| | 50 | 53.8 | 4.4 | 24.7 | 3.5 |

Trial 16: Citrus Rust Mite Test—Valencia Orange

Various compounds were foliar applied to selected branches of Valencia-variety orange trees for control of citrus rust mites. Applications were made to achieve a foliar spray of approximately 1000 gal/A.

The number of live mites were counted on 3 to 5 leaves and the results were recorded as percent control in Table XVI.

TABLE XVI

Citrus Rust Mite - Valencia Orange

| Example Number | Concentration (ppm) | Percent Control Days After Treatment | | | |
|---|---|---|---|---|---|
| | | 2-4 | 10-14 | 28-35 | 63 |
| 2 | 1000 | 97.6 | 96.8 | 52.9 | 98.5 |
| | 100 | 98.4 | 94.0 | 84.3 | 90.9 |
| 2(1EC) | 1000 | 100.0 | 100.0 | 100.0 | — |
| | 200 | 80.5 | 56.5 | 88.8 | — |
| | 100 | 35.1 | 0.0 | 38.2 | — |
| 2(1EC) | 300 | 97.7 | 90.7 | 40.7 | — |
| | 150 | 98.3 | 74.0 | 0.0 | — |
| 2(1 EC) | 1000 | 100.0 | 100.0 | 94.1 | 89.4 |
| | 100 | 98.0 | 96.3 | 92.1 | 77.3 |
| 2(50W) | 1000 | 80.5 | 100.0 | 49.4 | — |
| | 200 | 28.6 | 94.6 | 32.6 | — |
| | 100 | 80.5 | 78.3 | 0.0 | — |
| 2(50W) | 1000 | 95.9 | 98.6 | 0.0 | 100.0 |
| | 100 | 78.0 | 65.0 | 96.1 | 98.5 |
| 5 | 400 | 87.2 | 83.3 | 14.4 | — |
| | 200 | 85.5 | 55.5 | 75.3 | — |
| 6 | 1000 | 89.8 | 54.0 | 25.5 | 100.0 |
| | 100 | 94.3 | 85.7 | 0.0 | 0.0 |
| 7 | 1000 | 97.1 | 86.6 | 90.2 | 95.4 |
| | 100 | 96.7 | 98.1 | 100.0 | 0.0 |
| 8 | 1000 | 77.2 | 65.0 | 82.3 | 60.6 |
| | 100 | 86.6 | 60.9 | 86.3 | 100.0 |
| 11 | 1000 | 94.7 | 72.8 | 66.7 | 98.5 |
| | 100 | 63.8 | 42.0 | 84.3 | 100.0 |
| 13 | 1000 | 84.1 | 97.2 | 39.2 | 0.0 |
| | 100 | 78.9 | 56.7 | 54.9 | 90.6 |
| 14 | 1000 | 88.6 | 88.5 | 51.0 | 98.5 |
| | 100 | 90.6 | 98.1 | 100.0 | 92.4 |
| 15 | 1000 | 97.6 | 92.6 | 98.0 | 100.0 |
| | 100 | 84.1 | 34.2 | 0.0 | 89.4 |
| 16 | 1000 | 48.0 | 65.5 | 92.1 | 100.0 |
| | 100 | 35.8 | 14.4 | 98.0 | 100.0 |
| 18 | 1000 | 71.5 | 77.9 | 72.5 | 93.6 |
| | 100 | 75.2 | 95.8 | 100.0 | 100.0 |
| 19 | 1000 | 63.8 | 77.0 | 82.3 | 95.4 |
| | 100 | 63.8 | 48.5 | 96.1 | 100.0 |
| 20 | 1000 | 98.4 | 96.3 | 100.0 | 98.5 |
| | 100 | 90.2 | 74.2 | 92.1 | 87.9 |
| 21 | 1000 | 96.7 | 95.8 | 96.1 | 98.5 |

TABLE XVI-continued

Citrus Rust Mite - Valencia Orange

| Example Number | Concentration (ppm) | Percent Control Days After Treatment | | | |
|---|---|---|---|---|---|
| | | 2-4 | 10-14 | 28-35 | 63 |
| | 100 | 91.6 | 33.7 | 27.4 | 63.6 |
| 23 | 1000 | 98.8 | 85.7 | 64.7 | 100.0 |
| | 100 | 86.2 | 78.4 | 86.3 | 97.0 |
| 24 | 1000 | 39.8 | 66.9 | 52.9 | 12.1 |
| | 100 | 21.5 | 32.8 | 100.0 | 100.0 |
| 36 | 1000 | 100.0 | 100.0 | 94.4 | — |
| | 100 | 93.5 | 13.0 | 4.5 | — |
| 38 | 1000 | 100.0 | 83.7 | 100.0 | — |
| | 100 | 67.5 | 94.6 | 71.9 | — |
| 54 | 1000 | 0.0 | 0.0 | 0.0 | — |
| | 100 | 87.0 | 78.3 | 100.0 | — |
| 56 | 1000 | 93.5 | 94.6 | 71.9 | — |
| | 100 | 41.5 | 89.1 | 4.5 | — |
| 62 | 1000 | 80.5 | 0.0 | 88.8 | — |
| | 100 | 0.0 | 0.0 | 0.0 | — |
| 63 | 1000 | 22.1 | 0.0 | 94.4 | — |
| | 100 | 100.0 | 0.0 | 0.0 | — |
| 64 | 1000 | 22.1 | 0.0 | 60.7 | — |
| | 100 | 22.1 | 45.6 | 83.1 | — |

Trial 17: Citrus Rust Mite Test—Hamlin Orange

Compounds of this invention were foliar applied to selected branches of Hamlin-variety orange trees for control of citrus rust mite, using procedures described above. The results were recorded as percent control and are listed in the following Tables XVIIA–XVIIK.

TABLE XVIIA

Citrus Rust Mite - Hamlin Orange

| Example Number | Concentration (ppm) | Percent Control Days After Treatment | | |
|---|---|---|---|---|
| | | 4 | 14 | 49 |
| 1 | 80 | 37.1 | 63.5 | 87.1 |
| 2(1 EC) | 1000 | 100.0 | 100.0 | 55.3 |
| | 100 | 88.9 | 68.3 | 78.4 |
| | 50 | 68.6 | 89.2 | 20.9 |
| 2(50W) | 1000 | 72.8 | 91.0 | 41.5 |
| | 100 | 63.5 | 55.1 | 41.8 |
| | 50 | 91.5 | 81.4 | 22.2 |
| 3 | 1000 | 83.0 | 69.5 | 14.8 |
| | 100 | 88.1 | 61.7 | 31.5 |
| 9 | 1000 | 99.1 | 98.2 | 67.8 |
| | 100 | 12.5 | 56.3 | 38.3 |
| 10 | 1000 | 99.1 | 96.4 | 0.0 |
| | 100 | 98.3 | 94.0 | 26.7 |
| 17 | 1000 | 97.4 | 94.6 | 29.9 |
| | 100 | 78.8 | 56.3 | 73.9 |
| 22 | 1000 | 91.5 | 86.2 | 66.2 |
| | 100 | 88.9 | 18.0 | 22.5 |
| 25 | 1000 | 99.1 | 88.6 | 0.0 |
| | 100 | 99.1 | 86.2 | 6.1 |
| 37 | 1000 | 95.8 | 90.4 | 58.2 |
| | 100 | 59.2 | 89.2 | 30.5 |
| 44 | 1000 | 77.1 | 74.3 | 21.5 |
| | 100 | 66.9 | 0.0 | 11.9 |

TABLE XVIIB

Citrus Rust Mite - Hamlin Orange

| Example Number | Concentration (ppm) | Percent Control Days After Treatment | | |
|---|---|---|---|---|
| | | 4 | 14 | 49 |
| 2(1EC) | 1000 | 91.6 | 95.5 | 73.5 |
| | 200 | 94.4 | 90.9 | 46.1 |
| | 100 | 71.9 | 68.3 | 33.3 |
| | 50 | 42.4 | 69.3 | 0.0 |
| 2(50W) | 1000 | 96.5 | 96.0 | 58.8 |
| | 200 | 57.9 | 46.2 | 36.3 |
| | 100 | 42.4 | 37.7 | 61.8 |
| | 50 | 53.7 | 23.1 | 8.8 |
| 3 | 200 | 63.5 | 60.3 | 79.4 |
| | 100 | 53.7 | 78.4 | 76.5 |
| | 50 | 0.0 | 0.0 | 14.7 |
| 5 | 1000 | 88.8 | 86.9 | 61.8 |
| | 100 | 88.8 | 88.9 | 26.5 |
| 10 | 200 | 76.8 | 73.4 | 71.6 |
| | 100 | 60.0 | 70.3 | 48.0 |
| | 50 | 18.6 | 32.2 | 77.4 |

TABLE XVIIC

Citrus Rust Mite - Hamlin Orange

| Example Number | Concentration (ppm) | Percent Control Days After Treatment | | | |
|---|---|---|---|---|---|
| | | 4 | 14 | 28 | 52 |
| 2 | 200 | 93.8 | 81.0 | 85.1 | 81.9 |
| | 100 | 83.2 | 59.5 | 79.7 | 63.9 |
| | 75 | 81.4 | 65.8 | 52.7 | 41.3 |
| | 50 | 82.3 | 45.6 | 27.0 | 68.4 |
| 2(1 EC) | 200 | 61.1 | 79.7 | 77.0 | 84.2 |
| | 100 | 82.3 | 70.9 | 74.3 | 97.7 |
| | 75 | 56.6 | 69.6 | 71.6 | 61.6 |
| | 50 | 0.0 | 0.0 | 47.3 | 45.9 |
| 2(50W) | 200 | 59.3 | 87.3 | 90.5 | 63.9 |
| | 100 | 68.1 | 93.7 | 86.5 | 0.0 |
| | 75 | 48.7 | 57.0 | 20.3 | 81.9 |
| | 50 | 34.5 | 57.0 | 44.6 | 77.4 |
| 5 | 200 | 88.5 | 32.9 | 48.6 | 54.9 |
| | 100 | 95.6 | 81.0 | 63.5 | 27.8 |
| | 75 | 92.0 | 64.5 | 60.8 | 79.7 |
| | 50 | 66.4 | 51.9 | 0.0 | 52.6 |
| 7 | 200 | 92.0 | 67.1 | 91.9 | 93.2 |
| | 100 | 82.3 | 79.7 | 66.2 | 97.7 |
| | 75 | 83.2 | 87.3 | 63.5 | 97.7 |
| | 50 | 70.8 | 74.7 | 75.7 | 25.6 |
| 8 | 200 | 38.9 | 45.6 | 32.4 | 41.3 |
| | 100 | 51.3 | 27.8 | 39.2 | 77.4 |
| | 75 | 15.9 | 58.2 | 43.2 | 52.6 |
| | 50 | 49.5 | 57.0 | 0.0 | 66.2 |
| 10 | 200 | 90.3 | 83.5 | 82.4 | 81.9 |
| | 100 | 54.0 | 64.5 | 50.0 | 95.5 |
| | 75 | 41.6 | 68.3 | 28.4 | 34.6 |
| | 50 | 54.0 | 39.2 | 70.3 | 72.9 |
| 14 | 200 | 51.3 | 38.0 | 40.5 | 75.2 |
| | 100 | 64.6 | 41.8 | 44.6 | 81.9 |
| | 75 | 41.6 | 68.3 | 28.4 | 34.6 |
| | 50 | 0.0 | 25.3 | 0.0 | 59.4 |
| 37 | 200 | 70.8 | 79.7 | 83.8 | 91.0 |
| | 100 | 69.0 | 40.5 | 20.3 | 0.0 |
| | 75 | 0.0 | 63.3 | 43.2 | 34.6 |
| | 50 | 41.6 | 31.6 | 0.0 | 57.1 |
| 18 | 200 | 0.0 | 0.0 | 37.8 | 68.4 |
| | 100 | 0.0 | 0.0 | 0.0 | 0.0 |
| | 75 | 52.2 | 51.9 | 56.8 | 61.6 |
| | 50 | 45.1 | 55.7 | 59.4 | 75.2 |
| 20 | 200 | 83.2 | 72.1 | 66.2 | 27.8 |
| | 100 | 27.4 | 73.4 | 55.4 | 75.2 |
| | 50 | 48.7 | 38.0 | 0.0 | 23.3 |
| 22 | 200 | 47.8 | 53.2 | 54.0 | 54.9 |
| | 100 | 74.3 | 26.6 | 31.1 | 14.3 |
| | 75 | 78.8 | 54.4 | 50.0 | 91.0 |
| | 50 | 69.0 | 16.4 | 47.3 | 52.6 |
| 23 | 200 | 67.3 | 57.0 | 63.5 | 57.0 |
| | 100 | 56.6 | 70.9 | 0.0 | 91.0 |
| | 75 | 60.2 | 0.0 | 0.0 | 12.0 |
| | 50 | 55.8 | 58.2 | 24.3 | 79.7 |
| 25 | 200 | 91.1 | 67.1 | 86.5 | 77.4 |
| | 100 | 89.4 | 69.6 | 0.0 | 52.9 |
| | 75 | 67.3 | 34.2 | 0.0 | 63.9 |
| | 50 | 71.7 | 44.3 | 31.1 | 66.2 |

TABLE XVIID

Citrus Rust Mite - Hamlin Orange

| Example Number | Concentration (ppm) | Percent Control Days After Treatment | | |
|---|---|---|---|---|
| | | 5 | 14 | 28 |
| 2(1 EC) | 500 | 97.7 | 98.9 | 92.9 |
| | 200 | 97.7 | 88.3 | 86.7 |
| | 100 | 93.1 | 83.1 | 62.4 |
| 5 | 1000 | 97.7 | 98.4 | 96.0 |
| | 100 | 98.5 | 72.5 | 75.7 |
| 20 | 1000 | 91.5 | 98.5 | 97.3 |
| | 100 | 80.8 | 71.4 | 77.0 |
| 27 | 1000 | 80.0 | 100.0 | 94.3 |
| | 100 | 34.6 | 61.4 | 93.8 |

TABLE XVIIE

Citrus Rust Mite - Hamlin Orange

| Example Number | Concentration (ppm) | Percent Control Days After Treatment | | |
|---|---|---|---|---|
| | | 4 | 14 | 28 |
| 2(1 EC) | 200 | 84.7 | 74.5 | 31.8 |
| | 100 | 90.9 | 77.3 | 20.4 |
| 53 | 1000 | 55.6 | 56.2 | 37.6 |
| | 100 | 91.3 | 92.0 | 89.8 |
| 58 | 1000 | 74.9 | 34.3 | 8.3 |
| | 100 | 19.9 | 53.4 | 25.5 |
| 66 | 1000 | 70.7 | 26.7 | 39.5 |
| | 100 | 88.1 | 45.8 | 5.7 |

TABLE XVIIF

Citrus Rust Mite - Hamlin Orange

| Example Number | Concentration (ppm) | Percent Control Days After Treatment | | |
|---|---|---|---|---|
| | | 4 | 14 | 28 |
| 2(1 EC) | 300 | 94.9 | 90.6 | 0.0 |
| | 100 | 86.5 | 67.8 | 0.0 |
| 31 | 1000 | 69.1 | 92.7 | 81.3 |
| | 100 | 13.0 | 81.3 | 83.3 |
| 32 | 1000 | 95.4 | 87.9 | 97.9 |
| | 100 | 62.5 | 42.2 | 12.5 |
| 49 | 1000 | 0.0 | 90.3 | 85.4 |
| | 100 | 41.6 | 63.7 | 0.0 |
| 52 | 1000 | 87.0 | 93.8 | 50.0 |
| | 100 | 17.8 | 52.9 | 8.3 |
| 59 | 1000 | 39.5 | 87.2 | 0.0 |
| | 100 | 0.0 | 0.0 | 0.0 |
| 61 | 1000 | 23.2 | 83.4 | 0.0 |
| | 100 | 0.0 | 79.6 | 0.0 |
| 63 | 1000 | 63.3 | 74.0 | 0.0 |
| | 100 | 85.4 | 0.0 | 0.0 |
| 64 | 1000 | 55.6 | 50.9 | 18.7 |
| | 100 | 36.5 | 0.0 | 0.0 |
| 65 | 1000 | 36.2 | 40.5 | 16.7 |
| | 100 | 80.1 | 63.0 | 0.0 |
| 71 | 1000 | 71.4 | 21.4 | 0.0 |
| | 100 | 72.2 | 79.9 | 0.0 |
| 72 | 1000 | 5.9 | 81.3 | 58.3 |
| | 100 | 3.3 | 0.0 | 10.4 |

TABLE XVIIG

Citrus Rust Mite - Hamlin Orange

| Example Number | Concentration (ppm) | Percent Control Days After Treatment | | |
|---|---|---|---|---|
| | | 4 | 14 | 28 |
| 2(1 EC) | 300 | 86.7 | 89.6 | 97.6 |
| | 150 | 95.6 | 48.3 | 57.1 |
| 26 | 1000 | 99.4 | 98.3 | 100.0 |
| | 100 | 22.8 | 93.1 | 45.2 |
| 36 | 1000 | 81.6 | 82.8 | 88.1 |
| | 100 | 88.6 | 81.0 | 97.6 |
| 38 | 1000 | 93.0 | 72.4 | 88.1 |
| | 100 | 68.3 | 0.0 | 0.0 |
| 60 | 1000 | 82.9 | 86.2 | 61.9 |
| | 100 | 45.6 | 34.5 | 0.0 |
| 62 | 1000 | 68.3 | 36.2 | 71.4 |
| | 100 | 24.7 | 36.2 | 73.8 |
| 68 | 1000 | 64.5 | 70.7 | 50.0 |
| | 100 | 73.4 | 58.6 | 97.6 |
| 70 | 1000 | 76.6 | 0.0 | 42.8 |
| | 100 | 30.4 | 0.0 | 0.0 |

TABLE XVIIH

Citrus Rust Mite - Hamlin Orange

| Example Number | Concentration (ppm) | Percent Control Days After Treatment | |
|---|---|---|---|
| | | 5 | 16 |
| 2 (1 EC) | 300 | 98.4 | 84.1 |
| | 100 | 80.4 | 79.1 |
| 30 | 1000 | 91.2 | 84.5 |
| | 500 | 83.0 | 68.2 |
| | 100 | 0.0 | 0.0 |
| 34 | 1000 | 5.7 | 79.5 |
| | 500 | 51.5 | — |
| | 100 | 83.5 | — |
| 35 | 1000 | 0.0 | 31.9 |
| | 500 | 0.0 | — |
| | 100 | 0.0 | — |
| 42 | 1000 | 77.3 | 74.9 |
| | 500 | 7.7 | — |
| | 100 | 59.3 | — |
| 45 | 1000 | 9.8 | 64.5 |
| | 500 | 67.5 | — |
| | 100 | 0.0 | — |
| 48 | 1000 | 69.6 | 62.4 |
| | 500 | 24.2 | — |
| | 100 | 47.9 | — |
| 54 | 1000 | 7.7 | 26.9 |
| | 500 | 0.0 | — |
| | 100 | 24.2 | — |
| 56 | 1000 | 64.4 | 0.0 |
| | 500 | 76.8 | — |
| | 100 | 51.0 | — |
| 57 | 1000 | 15.5 | 44.8 |
| | 500 | 13.4 | — |
| | 100 | 0.0 | — |

TABLE XVIII

Citrus Rust Mite - Hamlin Orange

| Example Number | Concentration (ppm) | Percent Control Days After Treatment | |
|---|---|---|---|
| | | 5 | 14 |
| 2 (1 EC) | 100 | 21.5 | 58.1 |
| 33 | 1000 | 90.8 | 82.5 |
| | 500 | 80.0 | 68.6 |
| | 100 | 80.0 | 0.0 |
| 43 | 1000 | 95.4 | 93.0 |
| | 500 | 96.9 | 68.6 |
| | 100 | 76.9 | 65.1 |
| 55 | 1000 | 61.5 | 58.1 |
| | 500 | 81.5 | 23.3 |
| | 100 | 46.1 | 51.2 |

TABLE XVIIJ

Citrus Rust Mite - Hamlin Orange

| Example Number | Concentration (ppm) | Percent Control Days After Treatment |
|---|---|---|
| | | 5 |
| 2 (1 EC) | 200 | 99 |
| | 100 | 95 |
| 5 (1 EC) | 200 | 79 |
| | 100 | 57 |

TABLE XVIIJ-continued

| | Citrus Rust Mite - Hamlin Orange | |
|---|---|---|
| Example Number | Concentration (ppm) | Percent Control Days After Treatment 5 |
| 7 (1 EC) | 200 | 64 |
| | 100 | 70 |

TABLE XVIIK

| | Citrus Rust Mite - Hamlin Orange | | |
|---|---|---|---|
| Example Number | Concentration (ppm) | Percent Control Days After Treatment | |
| | | 5 | 13 |
| 2 | 100 | 94.5 | 98.3 |
| 5 | 200 | 81.3 | 95.0 |
| 7 | 200 | 56.3 | 83.5 |
| 40 | 1000 | 56.3 | 35.6 |
| | 500 | 0.0 | — |
| | 100 | 7.8 | — |
| 46 | 1000 | 57.0 | 85.1 |
| | 500 | 25.8 | 86.8 |
| | 100 | 35.1 | 50.4 |
| 47 | 1000 | 0.0 | 0.0 |
| | 500 | 68.0 | — |
| | 100 | 60.9 | — |
| 50 | 1000 | 58.6 | 70.3 |
| | 500 | 0.0 | 40.5 |
| | 100 | 6.3 | — |

Trial 18: Citrus Rust Mite Test—Grapefruit

Various compounds of this invention were foliar applied to Marsh-variety grapefruit trees moderately infested with citrus rust mites. One infested limb (approximately 2 cubic feet) was sprayed with 100 ml of compound solution. (The solution was prepared as described in previous trials.) The results were recorded as percent control after counting the number of mites on 3 leaves in Table XVIII. (The surface area of the leaves counted was from 1200–1800 sq. mm.)

TABLE XVIII

| | Citrus Rust Mite - Grapefruit | | | |
|---|---|---|---|---|
| Example Number | Concentration (ppm) | Percent Control Days After Treatment | | |
| | | 4 | 14 | 31 |
| 2 | 300 | 97.5 | 98.2 | 42.5 |
| | 200 | 86.2 | 90.0 | 81.0 |
| | 150 | 93.7 | 90.6 | 60.8 |
| | 100 | 96.5 | 96.5 | 52.9 |
| | 75 | 85.5 | 92.4 | 71.9 |
| 2 (1 EC) | 300 | 98.4 | 91.8 | 85.0 |
| | 200 | 89.3 | 91.2 | 90.2 |
| | 100 | 90.9 | 97.1 | 90.2 |
| | 75 | 94.0 | 90.0 | 90.2 |
| 5 (1 EC) | 500 | 99.4 | 88.3 | 88.9 |
| | 300 | 98.7 | 93.0 | 92.1 |
| | 100 | 68.9 | 84.8 | 71.2 |
| 7 | 300 | 84.3 | 85.4 | 58.8 |
| | 200 | 79.9 | 71.3 | 21.6 |
| | 150 | 60.4 | 91.8 | 77.8 |
| | 100 | 56.0 | 73.7 | 84.3 |
| | 75 | 82.1 | 78.9 | 50.3 |
| 10 | 300 | 96.2 | 93.0 | 66.7 |
| | 200 | 90.6 | 86.0 | 62.7 |
| | 150 | 92.1 | 83.6 | 92.8 |
| | 100 | 28.3 | 79.5 | 12.4 |
| | 75 | 73.6 | 62.0 | 0.0 |
| 37 | 300 | 84.3 | 60.2 | 89.5 |
| | 200 | 70.1 | 63.7 | 73.8 |
| | 150 | 39.3 | 20.5 | 0.0 |
| | 100 | 0.0 | 0.0 | 14.4 |
| | 75 | 70.1 | 68.4 | 0.0 |

Trial 19: Citrus Rust Mite Test—Grapefruit

Compounds of this invention were applied to Marsh-variety grapefruit trees as described in Trial 18, except the limb was sprayed with 90 ml of compound solution. The results are recorded in Table XIX.

TABLE XIX

| | Citrus Rust Mite-Grapefruit | | | | |
|---|---|---|---|---|---|
| Example Number | Concentration (ppm) | Percent Control Days After Treatment | | | |
| | | 3 | 10 | 21 | 35 |
| 2 (1 EC) | 200 | 73.0 | 68.4 | 68.4 | 82.5 |
| | 100 | 94.0 | 28.9 | 83.1 | 60.3 |
| 26 | 1000 | 61.0 | 92.1 | 92.1 | 76.2 |
| | 100 | 91.0 | 92.1 | 54.9 | 71.4 |
| 28 | 1000 | 73.0 | 28.9 | 91.0 | 38.1 |
| | 100 | 73.0 | 44.7 | 44.7 | 68.3 |
| 29 | 1000 | 88.0 | 84.2 | 91.0 | 63.5 |
| | 100 | 52.0 | 21.0 | 33.4 | 19.0 |
| 39 | 1000 | 19.0 | 0.0 | 43.6* | 47.6 |
| | 100 | 70.0 | 21.0 | 33.4 | 36.5 |
| 45 | 1000 | 73.0 | 0.0 | 69.5 | 14.3 |
| | 100 | 0.0 | 13.1 | 0.0 | 0.0 |

*Foliar injury

Trial 20: Citrus Rust Mite Test—Grapefruit

Some of the compounds of this invention were evaluated on Ruby-red-variety grapefruit trees infested with citrus rust mites. Approximately 5 gallons of compound solution were applied to the entire tree. The results were recorded as percent control based upon 3 replicates. In each replicate, the number of mites were counted on 5 fruit. (Each fruit had a surface area of about 12.5 sq. cm.)

TABLE XX

| | Citrus Rust Mite-Grapefruit | | | | |
|---|---|---|---|---|---|
| Example Number | Concentration (ppm) | Percent Control Days After Treatment | | | |
| | | 5 | 12 | 20 | 25 |
| 2 (1 EC) | 200 | 90.0 | 92.9 | 64.9 | 72.4 |
| | 100 | 53.8 | 77.2 | 58.9 | 94.5 |
| | 50 | 62.5 | 64.7 | 24.0 | 33.0 |
| 7 (1 EC) | 200 | 92.3 | 90.8 | 95.7 | 76.5 |
| | 100 | 87.3 | 87.0 | 32.9 | 74.7 |
| | 50 | 74.0 | 77.9 | 87.5 | 86.5 |
| 10 (1 EC) | 200 | 76.3 | 46.8 | 24.9 | — |
| | 100 | 61.1 | 29.8 | 0.0 | — |
| | 50 | 59.8 | 57.6 | 48.7 | — |
| 37 (1 EC) | 200 | 46.1 | 61.1 | 14.9 | — |
| | 100 | 55.4 | 46.7 | 50.1 | — |
| | 50 | 35.3 | 32.5 | 25.6 | — |

Trial 21: Citrus Red Mite Test—Valencia Orange

In this trial, compounds were evaluated for activity against the citrus red mite (*Panonychus citri*). The formulation for each test was poured into a hand-held sprayer. Individual branches of Valencia-variety orange trees were marked and sprayed with the formulation until the entire leaf surfaces were wet. At intervals of 2 and 6 days after treatment, 10 orange leaves were taken from the treated branches and 10 from the control branches, which had been sprayed with water. The entire leaf surfaces were examined under a dissecting microscope and the number of citrus red mites were counted. (Four replications were run.) The results are shown in Tables XXI and XXIA as percent control.

TABLE XXI

Citrus Red Mite-Valencia Orange

| Example Number | Concentration (ppm) | Percent Control Days After Treatment | |
|---|---|---|---|
| | | 2 | 4 |
| 2 | 500 | 0.0 | 0.0 |
| | 250 | 0.0 | 18.1 |
| | 100 | 0.0 | 0.0 |
| 7 | 500 | 0.0 | 0.0 |
| | 250 | 10.4 | 11.4 |
| | 100 | 0.0 | 2.0 |
| 10 | 500 | 53.6 | 22.4 |
| | 250 | 76.4 | 67.7 |
| | 100 | 37.7 | 46.4 |

TABLE XXIA

Citrus Red Mite - Valencia Orange

| Example Number | Concentration (lb/100 gal) | Percent Control Days After Treatment | | |
|---|---|---|---|---|
| | | 7 | 14 | 22 |
| 2 (1 EC) | 1 | 0.0 | 0.9 | 33.9 |
| | 2 | 32.2* | 0.0* | 46.1* |

| Example Number | Concentration (lb/100 gal) | Percent Control Days After Treatment | | | | | |
|---|---|---|---|---|---|---|---|
| | | 2 | 6 | 14 | 21 | 7$^a$ | 14$^a$ | 21$^b$ |
| 2 (1 EC) | 1 | 75.7 | 73.8 | 62.2 | 49.5 | 48.9 | 0.0 | 37.6 |
| | 2 | 54.0 | 75.3* | 27.8 | 13.6* | 31.5* | 0.0* | 0.0* |
| | 4 | 91.9 | 86.9* | 64.9 | 68.7* | 78.1* | 76.4* | 66.1* |

$^a$Second treatment.
$^b$Third treatment.
*Foliar injury.

Trial 22: Citrus Red Mite Test—Hamlin and Temple Orange

Compounds of this invention also were evaluated against citrus red mite as described above, but the evaluation was carried out on Hamlin-variety orange tree branches. Only 1 replication was run and the results were recorded on 4 and 19 days. The results are shown in Table XXII.

Evaluations were also conducted on Temple-variety orange trees, counting the mites on 5 fruit after 13 days. These results are recorded in Table XXIIA.

TABLE XXII

Citrus Red Mite - Hamlin Orange

| Example Number | Concentration (ppm) | Percent Control Days After Treatment | |
|---|---|---|---|
| | | 4 | 19 |
| 1 | 80 | 20.0 | 0.0 |
| 2 (1 EC) | 1000 | 100.0 | 100.0 |
| | 100 | 86.7 | 100.0 |
| | 50 | 73.3 | 0.0 |
| 2 (50W) | 1000 | 100.0 | 100.0 |
| | 100 | 100.0 | 85.2 |
| | 50 | 0.0 | 48.1 |
| 3 | 1000 | 86.7 | 48.1 |
| | 100 | 46.7 | 100.0 |
| 9 | 1000 | 100.0 | 85.2 |
| | 100 | 0.0 | 25.9 |
| 10 | 1000 | 100.0 | 100.0 |
| | 100 | 100.0 | 63.0 |
| 17 | 1000 | 100.0 | 77.8 |
| | 100 | 73.3 | 63.0 |
| 22 | 1000 | 86.7 | 70.4 |
| | 100 | 86.7 | 85.2 |
| 25 | 1000 | 100.0 | 48.1 |
| | 100 | 100.0 | 70.4 |

TABLE XXIIA

Citrus Red Mite - Temple Orange

| Example Number | Concentration (ppm) | Percent Control Days After Treatment 13 |
|---|---|---|
| 2 (1 EC) | 500 | 97.5 |
| | 200 | 92.4 |
| | 100 | 92.4 |
| 5 (1 EC) | 500 | 79.9 |
| | 200 | 82.4 |
| | 100 | 97.5 |
| 7 (1 EC) | 500 | 72.3 |
| | 200 | 79.9 |
| | 100 | 79.9 |
| 10 (1 EC) | 500 | 79.9 |
| | 200 | 17.0 |
| | 100 | 54.7 |

Trial 23: Apple Rust Mite Test

Various compounds were evaluated for the control of apple rust mite (*Aculus schlechtendali*) on detached apple branches. (The cut ends of the branches were placed in water during the test.) Infection was determined by examining a leaf from each branch.

Each compound was formulated by dissolving 10 mg in 1 ml of a solvent system, consisting of equal volumes of acetone and ethanol and small amounts of Toximul R and Toximul S equivalent to a concentration of 23 gm/l and 13 gm/l, respectively. The resulting solution was diluted with 9 ml of water to give 10 ml of solution, containing 1000 ppm of test compound. The solution was further diluted, where necessary, to give lower concentrations of compound.

The branches were sprayed to the point of run-off and rated 24 hours later. The number of mobile mites were counted on the first fully-expanded leaf of each branch and on the first hardened leaf of each branch. Counting ceased at 200 mites per leaf. The counts were converted to percent control and the percentages are recorded in Table XXIII.

Plant injury ratings were also made with 0 being no injury and 10 being severe injury.

TABLE XXIII

Apple Rust Mite

| Example Number | Concentration (ppm) | Percent Control | Plant Injury Rating |
|---|---|---|---|
| 2 | 1000 | 100 | 3.7 |
| | 500 | 100 | 3.3 |
| | 100 | 100 | 1.3 |
| 5 | 1000 | 100 | — |
| | 100 | 100 | — |
| | 50 | 100 | — |
| 6 | 1000 | 100 | — |
| | 100 | 100 | — |
| | 50 | 96 | — |
| 7 | 1000 | 100 | 3 |
| | 500 | 100 | 1 |
| | 100 | 100 | 0 |
| 8 | 1000 | 100 | — |
| | 100 | 99 | — |
| | 50 | 98 | — |
| 10 (1 EC) | 1000 | 82 | — |
| | 100 | 0 | — |
| 10 | 1000 | 91 | 1.3 |
| | 500 | 50 | 0.66 |
| | 100 | 0 | 0 |
| 10 | 1000 | 100 | — |
| | 100 | 76 | — |
| | 50 | 71 | — |
| 11 | 1000 | 94 | — |
| | 100 | 0 | — |
| | 50 | 0 | — |

TABLE XXIII-continued

| | Apple Rust Mite | | |
|---|---|---|---|
| Example Number | Concentration (ppm) | Percent Control | Plant Injury Rating |
| 12 | 1000 | 100 | — |
| | 100 | 51 | — |
| | 50 | 0 | — |
| 13 | 1000 | 0 | — |
| | 100 | 0 | — |
| | 50 | 0 | — |
| 15 | 1000 | 100 | — |
| | 100 | 100 | — |
| | 50 | 95 | — |
| 19 | 1000 | 0 | — |
| | 100 | 0 | — |
| | 50 | 0 | — |
| 20 | 1000 | 100 | — |
| | 100 | 91 | — |
| | 50 | 10 | — |
| 21 | 1000 | 100 | — |
| | 100 | 88 | — |
| | 50 | 81 | — |
| 23 | 1000 | 90 | — |
| | 100 | 0 | — |
| | 50 | 0 | — |
| 24 | 1000 | 90 | — |
| | 100 | 0 | — |
| | 50 | 0 | — |
| 25 | 1000 | 100 | — |
| | 100 | 93 | — |
| | 50 | 45 | — |
| 28 | 1000 | 100 | — |
| | 100 | 100 | — |
| | 50 | 100 | — |
| 29 | 1000 | 100 | — |
| | 100 | 100 | — |
| | 50 | 100 | — |
| 36 | 1000 | 78 | — |
| | 100 | 17 | — |
| | 50 | 0 | — |

Trial 24: Psoroptes Species Test

Normally, common scabies mites, *Psoroptes ovis* (Hering), were obtained from Government-owned cattle for these tests. During the summer months when these mites were not available, *Psoroptes cuniculi* (Delafond) taken from the ears of rabbits were used. About 20–25 adult or nymphal mites were put in 2.5×2.5-cm "teabags" made from heat-sealable rice paper. Usually the candidate acaricides were tested as technical materials formulated as emulsifiable concentrates, containing 25% active ingredient, 65% xylene, and 10% Triton X-100 (polyethylene glycol p-isooctylphenyl ether). Because of solubility problems, some materials were formulated as 10 or 20% ECs in xylene/Triton X-100 or in mixtures of N-methyl-2-pyrrolidone, xylene, and Triton X-100. Three bags containing mites were dipped in each concentration of the acaricide for 30 seconds and then allowed to dry at room temperature and ambient humidity. The bags were opened at 24 hours post-treatment, and the mites were observed with the aid of a dissecting microscope and classified as dead or alive. Mites scored as dead were immobile or had feeble leg movement. Mites scored as alive were able to travel in a normal manner. The mites that serve as controls were dipped in dilute solvent and emulsifier at concentrations equivalent to those used in acaricide emulsion.

The highest concentrations of acaricide tested was 0.1%. If 100% kill is obtained, more dilute concentrations (0.01%, 0.001%, 0.0001%, etc.) were tested until mortality is less than 100%. Acaricides were classified on the basis of the scoring as:

Class I: <100% kill at 0.01%
Class II: 100% kill at 0.1% and <100% kill at 0.01%
Class III: 100% kill at 0.01% and <100% kill at 0.001%
Class IV: 100% kill at 0.001% and <100% kill at 0.0001%
Class V: 100% kill at 0.0001%

The standard treatment, toxaphene, was rated as a Class V acaricide.

The test method is described by Wright and Riner, "A Method of Evaluating Acaricides for Control of Psoroptic Mites", *Southwest. Entomol.* 4(1): 40–45, (1979), which is hereby incorporated by reference. Previous acaricide evaluations were reported by Wright and Riner, 1979, *Insect. Acaric. Tests* 4: 213–214 (1979).

The compound of Example 2 was classified as Class II.

Trial 25: Spot Test for Animal Protectant Sprays

Candidate insecticides were screened as animal protectant sprays by the spot-test method. For a description of the development of the spot-test technique, see Roberts et al., "Methods for the evaluation of stable fly toxicants and repellents", *J. Econ. Entomol.* 53(2): 301-3, (1960) which is incorporated by reference. An area 6 inches (in.) in diameter on the side of a bovine (cow or steer) was sprayed with 5 ml of an acetone solution of the compound. During the winter months the hair on the area was clipped to $\frac{1}{4}$–$\frac{1}{2}$ in. in length so that the flies could reach the skin to feed, but clipping was not necessary when the animals were in summer coat. Five test areas, spaced on each side of an animal, were positioned so as to minimize cross-contamination. During the test period, the animals were confined in individual stanchions. Two sun lamps, 1 directed toward the treated spots on each side of a test animal, were turned on for a period of 4 hours each day. Each lamp was about 2 meters (m) from the floor and 1 m from the animal and positioned so that all treated spots received about the same amount of radiation.

Cages, made by soldering screen wire in a mason-jar ring, were used to confine adult stable flies, *Stomoxys calcitrans* (L.), to the treated spots. Twenty-five 3- to 6-day-old female flies that had not fed for about 18 hours were exposed to a spot for 20 minutes. Then the cage with the flies was removed and placed in the laboratory at 27° C. and 60–70% relative humidity. The number of flies that fed and the number that were knocked down were recorded, a square of cotton soaked in blood diet were placed on each cage, and the flies were held for 24 hours when mortality was recorded.

Compounds were tested for both repellency and toxicity at an initial concentration of 5%. Repellency was indicated when less than 20% of the flies had fed during the 20-minute exposure period. Toxicity was indicated when 90% or more of the flies were dead at 24 hours. Pyrethrins at 0.05%, which exhibit repellent activity for 4 days, and methoxychlor at 0.5%, which is effective at a toxicant for 8 days, were used as standards for comparison.

Compounds were rated according to the following classifications in Table XXV:

| Repellency | | Toxicity | |
|---|---|---|---|
| Class 1 | Ineffective at 1 day | Class 1 | Ineffective at 1 day |
| Class | Effective at 1 day | Class | Effective at 1 day |

| Repellency | | Toxicity | |
|---|---|---|---|
| II Class | Effective for 2-3 days | II Class | Effective for 4 days |
| III Class | Effective for 4 or more days | III Class | Effective for 8 or more days |
| IV | | IV | |

The compound was also reported as percent control in Table XXVA.

TABLE XXV

| | Spot Test | | |
|---|---|---|---|
| Example Number | Percent Concentration | Classification Toxicant | Repellent |
| 2 | 5 | I | II |

TABLE XXVA

| | | Spot Test | | | | |
|---|---|---|---|---|---|---|
| Example Number | Percent Concentration | Hours Posttreatment | No. flies Exposed | Killed | Knock-Down | Repelled |
| 2 | 0.5 | 24 | 25 | 4 | 0 | 100 |
| | | 96 | 25 | 0 | 0 | 60 |
| | | 24 | 24 | 8 | 0 | 100 |
| | | 96 | 25 | 0 | 4 | 40 |
| | | 168 | 25 | 0 | 0 | 12 |

Trial 26: Special Spot Test

To further test the ability of a material to inhibit feeding of stable flies, spots on a steer were treated as above and the flies were exposed at 1, 2, 4, 6, 24 hours, etc. posttreatment. In the first treatment, acetone only and 50% deet in acetone were used as controls, and other spots were treated with acetone solutions of 5%, 0.5%, and 0.05% of the compound of Example 2. The second and third treatment included 5% rather than 50% deet. Since some of the test material was removed with the test cages at each exposure, several spots were treated with the 0.05% of compound and flies were exposed to a different spot at each time interval.

TABLE XXVI

| | Stable Flies - Special Spot Tests | | | | | | | | | | |
|---|---|---|---|---|---|---|---|---|---|---|---|
| Hours post-treatment | Untreated | | Acetone | | Deet | | Example No. 2 | | | | |
| | | | | | | | 5% | | 0.5% | | 0.05% |
| | R | K | R | K | R | K | R | K | R | K | R | K |
| First Treatment | | | | | | | | | | | | |
| 1 | | | 4 | 0 | 100 | 100 | 100 | 4 | 100 | 72 | 68 | 20 |
| 2 | | | 4 | 0 | 100 | 100 | 100 | 8 | 100 | 4 | 68 | 0 |
| 4 | | | 0 | 0 | 100 | 100 | 100 | 0 | 100 | 4 | 56 | 0 |
| 6 | | | 8 | 0 | 100 | 100 | 96 | 4 | 92 | 0 | 56 | 4 |
| 24 | | | 0 | 4 | 100 | 100 | 32 | 0 | 52 | 0 | 32 | 0 |
| 48 | | | 8 | 0 | 75 | 83 | 36 | 0 | 44 | 0 | 20 | 0 |
| Second Treatment | | | | | | | | | | | | |
| 1 | 0 | 0 | 8 | 0 | 52 | 67 | 67 | 20 | | | 28 | 36 |
| 2 | — | — | — | — | 56 | 88 | — | — | | | 28 | 16 |
| 4 | 0 | 8 | 0 | 8 | 56 | 100 | 60 | | | | 52 | 16 |
| 6 | 4 | 8 | 0 | 8 | 64 | 92 | 72 | 0 | | | 32 | 24 |
| 24 | 8 | 4 | 4 | 8 | 20 | 28 | 15 | 25 | | | 4 | 0 |
| Third Treatment | | | | | | | | | | | | |
| 1 | 4 | 0 | 0 | 0 | 100 | | 100 | 0 | 88 | 12 | 84 | 0 |
| 2 | — | — | — | — | 100 | | 100 | 4 | 92 | 0 | 56 | 4 |
| 4 | — | — | — | — | 100 | | 88 | 8 | 76 | 16 | 68 | 0 |
| 6 | 0 | 0 | 0 | 4 | 96 | | 80 | 4 | 64 | 4 | 40 | 0 |
| 24 | 16 | 0 | 4 | 8 | 32 | | 20 | 8 | 68 | 0 | 52 | 0 |

R = repelled.
K = killed.

Trial 27: Reproduction of One-Host Ticks

Larvae of *Boophilus annulatus* (Say), the cattle tick, and *B. microplus* (Oanestrini), the southern cattle tick, in colony at Falcon Heights, TX, and *Anocentor nitens* (Neumann), the tropical horse tick, and *Dermacentor albipictus* (Packard), the winter tick, at Kerrville, TX, were placed onto cattle, and engorged females that detach naturally were used in the following screening test.

Usually candidate compounds were formulated as emulsifiable concentrates containing 25% active ingredient, 65% xylene, and 10% Triton X-100. Compounds not soluble in xylene were formulated in mixtures of N-methyl-2-pyrrolidone, xylene, and Triton X-100. All formulations were mixed with water immediately before treatment. Acaricides were routinely tested at 1%, 0.1%, and 0.01% active ingredient; the lesser concentrations were obtained by serial dilution of the 1% concentration. For use as controls, groups of 10 ticks were dipped in an emulsion of 2.6% xylene and 0.4% Triton X-100.

Ticks were washed, dried, sorted into groups of 10, weighed, and placed into 45-50 ml of acaricide, which was stirred vigorously for 30 seconds and then poured through a screen that retained the ticks. After draining, the ticks were placed on paper toweling to dry and then were held in 8-dram shell vials at 27±1° C. and greater than 80% relative humidity for oviposition. After 2-3 weeks, the ticks were discarded; the eggs were weighed and held for another month when percentage hatch was estimated visually.

Effectiveness was determined by comparing the estimated reproduction (AR) of each group of treated ticks with that of the control ticks. First ER was calculated as follows:

$$ER = \frac{\text{wt. eggs laid (g)}}{\text{wt. females (g)}} \times \text{est. hatch (\%)} \times 20{,}000 \text{ larvae}$$

Second ER of each group of treated ticks was compared with that of its control group, to find the percentage control, as follows:

$$\text{Control (\%)} = \frac{ER \text{ control ticks} - ER \text{ treated ticks}}{ER \text{ control ticks}} \times 100$$

An acaricide was considered effective if the ER of treated ticks is less than 10% of that of control ticks (90% inhibition of ER). By this criterion, acaricides were placed in the following classes:

Class 1: Ineffective at 1%
Class 2: Effective at 1%
Class 3: Effective at 0.1%
Class 4: Effective at 0.01%

The compound of Example 2 was in Class 1 for all species when the compound was formulated as a 12.5% emulsifiable concentrate.

Trial 28: Whole-body Spray on Stable and Horn Flies

The compound of Example No. 2 was tested as a whole-body spray. For this test the material was applied in a water mixture with a compressed air garden sprayer. A 2.5% mixture was prepared by adding 25 g of compound to a mixture of 25 ml methyl pyrrolidinone and 75 ml of a solution that was 65 parts xylene and 10 parts Triton X-100, and this was mixed with 875 ml water and applied to a steer. When the animal was dried sufficiently it was put in a 10-foot-square indoor cage and 100 unfed mature stable flies and 200 unfed mature horn flies were released in the cage at 4 and 24 hours posttreatment. An untreated steer was used for a control. After 2 hours of exposure, the surviving stable flies in each cage were recaptured, examined to determine the number fed, and held as above for 24 hours before the dead were counted. The effects of exposure on the horn flies was determined by estimating the number of flies remaining on the steer 24 hours after release. The results are reported in Table XVIII.

(The compound in this formulation was very irritating to the steer.)

TABLE XVIII

| Hours posttreatment | Whole-body Spray - Stable and Horn Flies | | | |
|---|---|---|---|---|
| | No. stable flies[a] | | | No. horn flies[b] |
| | Captured | Fed | Dead @ 24 hr | Dead @ 24 hr |
| | Treated | | | |
| 4 | 91 | 91 | 34 | 185 |
| 24 | 91 | 90 | 0 | 155 |
| | Untreated | | | |
| 4 | 87 | 87 | 0 | 20 |
| 24 | 93 | 92 | 4 | — |

[a]Released 100 stable flies.
[b]Released 200 horn flies.

Trial 29: Cabbage Looper—Soybean

The compound of Example 2 was foliar applied at the rate of 1000 ppm to Jupiter-variety soybeans for the control of cabbage looper (*Trichoplusia ni*) larvae. The application was made to the point of run-off using a handgun at 5 lb. per sq. in. The number of living larvae was counted 5 days after treatment and the percent control calculated as 22.2%. The compound was also phytotoxic, causing leaf burn.

Trial 30: Red Imported Fire Ant

The compound of Example 9 was evaluated against imported fire ants (*Solenopsis invicta*). The tests were conducted with fire ant mounds in Coastal-variety bermudagrass. The compound was formulated as a bait using refined soybean oil and corn grits with the compound being 0.3, 0.5, or 1% of the bait. The bait was supplied to 5 fire-ant mounds in each test and the results were recorded in terms of percent control of adult ants in Table XXX.

TABLE XXX

| Red Imported Fire Ant | | | |
|---|---|---|---|
| Concentration (Percent) | Dosage (oz/mound) | Days After Treatment | Percent Control |
| 0.3 | 1 | 4 | 0.0 |
| | | 7 | 10.0 |
| | | 14 | 10.0 |
| 0.3 | 3 | 4 | 0.0 |
| | | 7 | 18.0 |
| | | 14 | 10.0 |
| 0.5 | 1 | 17 | 0.0 |
| | | 31 | 0.0 |
| | | 49 | 0.0 |
| 1.0 | 1 | 17 | 20.0 |
| | | 31 | 0.0 |
| | | 49 | 0.0 |

Trial 31: Corn Root Worm Larvicide

Thirty grams of non-sterile soil, 2 ml of distilled water, and 1 kernel of seed corn were placed in a cup. One ml or less of a 300 ppm solution of the compound was added to the cup and incorporated into the soil. (The addition of one ml of solution resulted in a concentration of 10 ppm.) The corn seed was covered by the soil. Five second-instar larvae of the Southern corn rootworm (*Diabrotica undecimpunctata howardi*) were added to the cup, which then is covered with a petri dish. Two replicates were employed.

The cup was maintained under fluorescent lights at room temperature. An observation was made from 2–4 days after treatment. The soil was then poured into a modified Berlese funnel, which had a screen placed 1 in. down from its rim. A heat lamp (250 watts) was used to force the larvae down through the screen to a collecting beaker. Two hours after the lamp was turned on, the number of larvae found in the beaker was counted.

The larva count was recorded as percent control. The results are recorded in Table XXXI.

TABLE XXXI

| Example Number | Corn Rootworm | | |
|---|---|---|---|
| | Concentration (ppm) | Mean Percent Control | Days After Treatment |
| 10 | 10 | 30 | 2 |
| | 10 | 10 | 2 |
| 2 | 10 | 40 | 4 |
| | 5 | 0 | 4 |
| | 2.5 | 0 | 4 |
| | 1.25 | 0 | 4 |
| 5 | 10 | 90 | 2 |
| | 10 | 40 | 2 |
| | 5 | 20 | 2 |
| | 5 | 40 | 2 |
| | 1 | 0 | 2 |
| 12 | 10 | 30 | 2 |
| 14 | 10 | 0 | 2 |
| 7 | 10 | 0 | 4 |
| | 5 | 0 | 4 |
| | 2.5 | 0 | 4 |
| | 1.25 | 0 | 4 |
| 15 | 10 | 0 | 4 |
| 16 | 10 | 0 | 4 |
| 17 | 10 | 100 | 4 |
| | 10 | 100 | 4 |
| | 5 | 50 | 4 |
| | 2.5 | 20 | 4 |
| | 1.25 | 0 | 4 |
| 18 | 10 | 0 | 4 |
| 21 | 10 | 0 | 4 |
| 33 | 10 | 0 | 3 |
| 34 | 10 | 0 | 4 |
| | 10 | 0 | 4 |
| 30 | 10 | 0 | 4 |

Trial 32: Cotton Bollworm Test

Fifteen milligrams of each test compound was dissolved in 1 ml of solvent. (The solvent was a 1/1 acetone and water system, which also contained 1.174 g of Toximul R and 0.7838 g of Toximul S per liter.) The mixture was diluted to produce various concentrations of test compound. First instar bollworms (*Heliothis zea*) were placed in a petri dish containing filter paper and then treated with 2 ml of test compound solution. Ten bollworms were placed per dish with 2 replications. The bollworms were allowed to remain in the dish for 1 hour and then were transferred to media cups.

Ovicidal activity also was tested by treating eggs laid on cheesecloth (20 eggs per treatment) with test compound for 2 hours. The eggs were transferred to a cup containing moist cotton and allowed to hatch.

Observations were made at 24 and 48 hours after treatment for larvae, while observations were made after complete hatch of the control eggs for ovicidal activity, usually 3-5 days after treatment.

The results were recorded as percent control in Table XXXII.

TABLE XXXII

| Example Number | Concentration (ppm) | Days After Treatment | Percent Control Ovicide | Percent Control Mobile |
|---|---|---|---|---|
| 5 | 500 | 5 | 94 | |
|   | 100 | 5 | 94.5 | |
|   | 10  | 5 | 70 | |
| 5 | 500 | 1 |    | 80 |
|   | 500 | 1 |    | 80 |
|   | 100 | 1 |    | 80 |
|   | 100 | 1 |    | 80 |
|   | 10  | 1 |    | 0 |
|   | 10  | 1 |    | 0 |
| 5 | 500 | 2 |    | 80 |
|   | 500 | 2 |    | 80 |
|   | 500 | 2 |    | 80 |
|   | 100 | 2 |    | 80 |
|   | 100 | 2 |    | 80 |
|   | 100 | 2 |    | 80 |
|   | 10  | 2 |    | 0 |
|   | 10  | 2 |    | 0 |
|   | 10  | 2 |    | 0 |
| 8 | 500 | 5 | 3.5 | |
|   | 100 | 5 | 0 | |
|   | 10  | 5 | 0 | |
| 8 | 500 | 1 |    | 10 |
|   | 500 | 1 |    | 10 |
|   | 500 | 2 |    | 10 |
|   | 500 | 2 |    | 10 |
|   | 500 | 2 |    | 10 |
| 12 | 500 | 5 | 2.5 | |
|    | 100 | 5 | 7 | |
|    | 10  | 5 | 0 | |
| 12 | 500 | 1 |    | 0 |
|    | 500 | 1 |    | 0 |
|    | 500 | 2 |    | 0 |
|    | 500 | 2 |    | 0 |
|    | 500 | 2 |    | 0 |
| 14 | 500 | 5 | 45 | |
|    | 100 | 5 | 24.5 | |
|    | 10  | 5 | 49.5 | |
| 14 | 500 | 1 |    | 20 |
|    | 500 | 2 |    | 20 |
|    | 500 | 2 |    | 20 |
| 33 | 500 | 1 |    | 10 |
|    | 500 | 2 |    | 20 |
|    | 500 | 4 | 0 | |

Formulations

The present compounds are employed in manners conventional to known insecticides and arachnicides. A compound or compounds in accordance with the present invention is typically formulated with an adjuvant, which is agriculturally acceptable, to facilitate the present use of the compound or compounds. Thus, there can be employed as an adjuvant: water, an organic solvent, a surface active dispersing agent, an inert finely-divided solid, a propellant (as in an aerosol), a sticker which will insure adherence of a treating formulation to foliage, and the like. The use of a surface-active dispersing agent is generally preferred with the formulations suitably contain from 0.1 to 95% of the present active agent.

Insecticides and miticides are generally applied in the form of a dispersion of the active ingredient in a liquid carrier. It is conventional to refer to application rates in terms of the concentration of active ingredient in the carrier. The most widely used carrier is water. Aqueous dispersions are usually prepared by mixing a small amount of a concentrated composition with an appropriate quantity of water to give the desired concentration. The concentrated compositions, before being dispersed in water, are usually in the form of emulsifiable concentrates or wettable powders containing from about 5 to about 90% of the compound.

Wettable powders comprise a mixture of the active compound in an inert carrier, which itself is a mixture of a fine inert powder and surfactants. The concentration of the active compound is usually from about 10 to about 90% by weight. The inert powder is usually chosen from among the attapulgite clays, the montmorillonite clays, the diatomaceous earths, or the purified silicates. Effective surfactants, comprising from about 0.5 to about 10% of the wettable powder, are found among the sulfonated lignins, the condensed naphthalenesulfonates, the naphthalenesulfonates, the alkylbenzenesulfonates, the alkyl sulfates, and nonionic surfactants, such as ethylene oxide adducts of alkyl phenol.

| Wettable Powder (50 W) | |
|---|---|
| Ingredients | Percent by Weight |
| Compound of Example 2 | 51.5 |
| Stepanol ME (sodium lauryl sulfate) | 5.0 |
| Polyfon 0 (sulfonated lignin) | 5.0 |
| Zeolex-7 (sodium silica aluminate) | 5.0 |
| Bardens Clay | 33.5 |
|  | 100.0 |

The above ingredients were blended to uniformity and the particle size was reduced by grinding in an appropriate hammer or air mill. The powder was then reblended to give a homogeneous free-flowing product.

Typical emulsifiable concentrates of the compounds comprise a convenient concentration of the compound, such as from about 50 to about 500 grams per liter of liquid, equivalent to from about 5% to about 50%, dissolved in an inert carrier, which is a mixture of water-immiscible organic solvent and emulsifiers. Useful organic solvents include the aromatics, especially the xylenes and acetophenone, and the petroleum fractions, especially the high-boiling naphthalenic and olefinic portions of petroleum such as heavy aromatic naphtha. Other organic solvents may also be used, such as the terpenic solvents including rosin derivatives, and complex alcohols such as 2-ethoxyethanol. Suitable emulsifiers for emulsifiable concentrates are chosen from the same types and concentrations of surfactants used for wettable powders.

| Emulsifiable Concentrate (1 lb/gal) (1 EC) | |
| --- | --- |
| Ingredient | Percent by Weight |
| Compound of Example 2 | 12.5 |
| Toximul D (sulfonate-nonionic blend of emulsifiers) | 5.0 |
| Toximul H (sulfonate-nonionic blend of emulsifiers) | 5.0 |
| Acetophenone | 77.5 |
| | 100.0 |

The above-listed ingredients were blended together to form the concentrate.

It is equally practical, when desirable for any reason, to apply the compound in the form of a solution in an appropriate organic solvent, usually a bland petroleum oil, such as the spray oils, which are widely used in agricultural chemistry.

Further, the compounds may be applied as compositions in the forms of dusts and aerosol preparations. Dusts comprise a compound in a finely powdered form, dispersed in a powdered inert carrier. The carrier is usually a powdered clay, such as pyrophyllite, bentonite, a volcanic deposit, or montmorillonite. Dusts usually contain concentrations of the compound in the range of from about 0.1 to about 10%.

The insecticidal and miticidal compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

Other formulations were prepared as follows:

| Ingredients | Percent by Weight |
| --- | --- |
| Bait | |
| Compound of Example 9 | 1.0 |
| Soybean oil | 16.0 |
| Corn cob grits | 83.0 |
| | 100.0 |
| Emulsifiable Concentrate (1 lb/gal) (1 EC) | |
| Compound of Example 7 | 12.5 |
| Toximul D | 5.0 |
| Toximul E | 5.0 |
| Acetophenone | 77.5 |
| | 100.0 |
| Compound of Example 10 | 12.5 |
| Toximul D | 5.0 |
| Toximul H | 5.0 |
| Acetophenone | 77.5 |
| | 100.0 |
| Compound of Example 37 | 12.5 |
| Toximul D | 5.0 |
| Toximul H | 5.0 |
| Acetophenone | 77.5 |
| | 100.0 |
| Compound of Example 5 | 12.5 |
| Toximul H | 10.0 |
| Acetophenone | 77.5 |
| | 100.0 |

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species also provides exemplification of the wide range of settings in which the present compounds can be used.

Because of the unique ability of mite eggs to resist toxicant action, repeated applications may be desirable to control newly emerged larvae, as is true of other known acaricides.

Some of the compounds to be employed in the above described insecticidal and arachnicidal uses also exhibit ectoparasiticidal activity when applied to the locus of ectoparasites on the surface of warm blooded host animals.

Parasitic insect and acarina are legion and include species which are bloodsucking as well as flesh eating, and species which are parasitic during all of their life cycle or only part of their life cycle, such as only the larval or only the adult stage. Representative species include the following:

| Parasites of Horses | |
| --- | --- |
| horsefly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| Parasites of Bovines | |
| horn fly | Haematobia irritans |
| cattle biting louse | Bovicola bovis |
| short-nosed cattle louse | Haematopinus eurysternus |
| long-nosed cattle louse | Linognathus vituli |
| tsetse fly | Glossina spp. |
| stable fly | Stomoxys calcitrans |
| horse fly | Tabanus spp. |
| cattle follicle mite | Demodex bovis |
| scab mite | Psoroptes ovis |
| cattle tick | Boophilus microplus and decoloratus |
| Gulf Coast tick | Amblyomma maculatum |
| Lone-Star tick | Amblyomma americanum |
| ear tick | Otobius megnini |
| Rocky Mountain spotted fever tick | Demacentor andersoni |
| blowfly larva | Callitroga hominivorax |
| assassin bug | Reduvius spp. |
| mosquito | Culiseta inornata |
| brown ear tick | Rhipicephalus appendiculatus |
| red-legged tick | Rhipicephalus evertsi |
| bont tick | Amblyomma sp. |
| bont legged tick | Hyalomma sp. |
| Parasites of Swine | |
| hog louse | Haematopinus suis |
| chigoe flea | Dermatophilus penetrans |
| Parasites of Sheep and Goats | |
| bloodsucking body louse | Haematopinus ovillus |
| bloodsucking foot louse | Linognathus pedalis |
| sheep ked | Melophagus ovinus |
| scab mite | Psoroptes ovis |
| greenbottle fly | Lucilia serioata |
| black blowfly | Phormia regina |

| | |
|---|---|
| secondary screw-worm | *Callitroga macellaria* |
| sheep blowfly | *Lucilia cuprina* |
| Parasites of Poultry | |
| bed bug | *Cimex lectularius* |
| Southern chicken flea | *Echidnophaga gallinacea* |
| fowl tick | *Argas persicus* |
| chicken mite | *Dermanyssus gallinae* |
| scaly-leg mite | *Knemidokoptes mutans* |
| depluming mite | *Knemidokoptes gallinae* |
| Parasites of Dogs | |
| horse fly | *Tabanus spp.* |
| stable fly | *Stomoxys calcitrans* |
| manage mite | *Sarcoptes scabiei* |
| dog follicle mite | *Demodex canis* |
| dog flea | *Ctenocephalis canis* |
| American dog tick | *Demacentor variabilis* |
| brown dog tick | *Rhipicephalus sanguineus* |

Although the parasites are listed above as associated with a particular host, in fact the various parasites freely attack other animals as well.

The rate, timing, and manner of effective application will vary widely with the identity of the parasite, the degree of parasiticidal attack, and other factors. The compounds can be applied to the surface of host animals by spray, dip, spot application, or drench, utilizing a liquid formulation containing the compound. The compounds can also be applied in dusts, which can be applied to the surface of animals or supplied to the animals in dust bags or as "back rubbers" for optional use by the animals. Application can be made periodically over the entire lifespan of the host, or for only a peak season of parasitic attack. In genral, ectoparasite control is obtained with liquid formulations containing from about 0.00005 to 5.0% of compound, and preferably from about 0.00005 to about 1.0% of compound.

For application to host animals, the present compounds are formulated in conventional manners, with one or more physiologically acceptable adjuvants, which can be any substance that aids in the implementation of the ectoparasiticidal activity of the compounds. The adjuvant can be a solvent, an inert diluent, a surface active agent, a suspending agent, and the like.

We claim:

1. A compound of the formula (I):

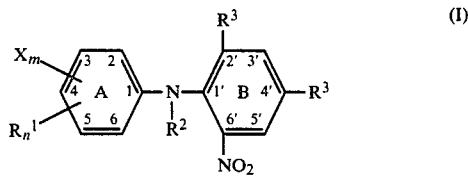

wherein:
 $R^1$ is nitro, cyano, or trifluoromethyl;
 $R^2$ is hydrogen or methyl;
 one $R^3$ is nitro and the other $R^3$ is $C_3$–$C_6$ alkyl or $C_3$–$C_6$ cycloalkyl;
 X is halo;
 m is an integer of from 0 to 5; and
 n is an integer of from 0 to 2;
provided that:
 (a) not more than one of $R^1$ is cyano;
 (b) when $R^1$ is trifluoromethyl, $R^1$ cannot also be nitro;
 (c) when X is iodo, m cannot be greater than 3 and the iodos cannot be on adjacent carbons;
 (d) at least one of m and n must be greater than 0, but the sum of m and n cannot be greater than 5; and
 (e) $R^2$ cannot be methyl when the 2 and 6 positions of ring A are both substituted by groups other than fluorine or hydrogen.

2. The compound of claim 1 wherein $R^3$ in the para position is nitro and $R^3$ in the ortho position is tertiary butyl.

3. The compound of claim 2 wherein $R^2$ is hydrogen, X is chloro, fluoro, or bromo, m is 3, and n is 0.

4. The compound of claim 3 which is 2,4,6-trichloro-2'-t-butyl-4',6'-dinitrodiphenylamine.

5. The compound of claim 3 which is 2,4,6-tribromo-2'-t-butyl-4',6'-dinitrodiphenylamine.

6. The compound of claim 2 wherein $R^2$ is hydrogen, $R^1$ is nitro, n is 2, and m is 0.

7. The compound of claim 6 which is 2,4-dinitro-2'-t-butyl-4',6'-dinitrodiphenylamine.

8. The compound of claim 2 which is 4-trifluoromethyl-2'-t-butyl-4',6'-dinitrodiphenylamine.

9. The compound of claim 1 wherein $R^3$ in the para position is tertiary butyl and $R^3$ in the ortho position is nitro.

10. The compound of claim 9 which is 2,4,6-trichloro-4'-t-butyl-2',6'-dinitrodiphenylamine.

11. A formulation which comprises a compound of claim 1 together with an agriculturally-acceptable carrier therefor.

12. The formulation of claim 11 wherein $R^3$ in the para position is nitro and $R^3$ in the ortho position is tertiary butyl.

13. The formulation of claim 12 wherein $R^2$ is hydrogen, X is chloro, fluoro, or bromo, m is 3, and n is 0.

14. The formulation of claim 13 wherein the compound is 2,4,6-trichloro-2'-t-butyl-4',6'-dinitrodiphenylamine.

15. The formulation of claim 13 wherein the compound is 2,4,6-tribromo-2'-t-butyl-4',6'-dinitrodiphenylamine.

16. The formulation of claim 12 wherein $R^2$ is hydrogen, $R^1$ is nitro, n is 2, and m is 0.

17. The formulation of claim 16 wherein the compound is 2,4-dinitro-2'-t-butyl-4',6'-dinitrodiphenylamine.

18. The formulation of claim 12 wherein the compound is 4-trifluoromethyl-2'-t-butyl-4',6'-dinitrodiphenylamine.

19. The formulation of claim 11 wherein $R^3$ in the para position is tertiary butyl and $R^3$ in the ortho position is nitro.

20. The formulation of claim 19 wherein the compound is 2,4,6-trichloro-4'-t-butyl-2',6'-dinitrodiphenylamine.

* * * * *

UNITED STATES PATENT AND TRADEMARK OFFICE
CERTIFICATE OF CORRECTION

PATENT NO. : 4,670,596

DATED : June 2, 1987

INVENTOR(S) : Barry A. Dreikorn, et al.

It is certified that error appears in the above—identified patent and that said Letters Patent is hereby corrected as shown below:

Column 59, lines 58-59, that portion which reads
"$C_3$-$C_6$ alkyl or $C_3$-$C_6$ cycloalkyl;" should read --tert-butyl;--.

Signed and Sealed this

Seventeenth Day of November, 1987

Attest:

DONALD J. QUIGG

*Attesting Officer*    *Commissioner of Patents and Trademarks*